(12) United States Patent
Ren et al.

(10) Patent No.: US 12,268,689 B2
(45) Date of Patent: Apr. 8, 2025

(54) EUTECTIC FORM A OF ELAGOLIX AND PYRIMETHAMINE, PREPARATION METHOD THEREFOR AND USE THEREOF

(71) Applicant: Shenzhen Rentai Pharmatech Ltd., Shenzhen (CN)

(72) Inventors: Guobin Ren, Shenzhen (CN); Weijie Ji, Shenzhen (CN); Dongxu Yi, Shenzhen (CN); Jiajun Huang, Shenzhen (CN)

(73) Assignee: SHENZHEN JINGTAI TECHNOLOGY CO., LTD, Guangdong (CN)

( * ) Notice: Subject to any disclaimer, the term of this patent is extended or adjusted under 35 U.S.C. 154(b) by 723 days.

(21) Appl. No.: 17/586,160

(22) Filed: Jan. 27, 2022

(65) Prior Publication Data

US 2022/0143019 A1    May 12, 2022

Related U.S. Application Data

(63) Continuation of application No. PCT/CN2019/098642, filed on Jul. 31, 2019.

(51) Int. Cl.
*A61K 31/513*     (2006.01)
*A61K 31/505*     (2006.01)

(52) U.S. Cl.
CPC .......... *A61K 31/513* (2013.01); *A61K 31/505* (2013.01)

(58) Field of Classification Search
CPC ........................... A61K 31/505; A61K 31/513
See application file for complete search history.

(56) References Cited

U.S. PATENT DOCUMENTS

2005/0038057 A1    2/2005  Guo et al.

FOREIGN PATENT DOCUMENTS

| CN | 100424078 C | 8/2008 |
| CN | 104398517 A | 3/2015 |
| IN | 1819829 A | 8/2006 |
| WO | 2005007165 A1 | 1/2005 |
| WO | 2017221144 A1 | 12/2017 |
| WO | 2018189212 A1 | 10/2018 |
| WO | 2018224063 A2 | 12/2018 |

OTHER PUBLICATIONS

International Search Report and Written Opinion mailed Apr. 24, 2020 in reference to co-pending Chinese Patent Application No. PCT/CN2019/098642 filed Jul. 31, 2019.
Chinese Office Action in reference to Chinese Application No. 201900022590 filed Mar. 28, 2022.

*Primary Examiner* — James D. Anderson
(74) *Attorney, Agent, or Firm* — Dinsmore & Shohl LLP

(57) ABSTRACT

Disclosed are eutectic form A of Elagolix and pyrimethamine, a preparation method therefor and a use thereof. Using Cu-Kα radiation, eutectic form A has characteristic peaks represented by a 2θ degree at 8.1±0.2°, 12.2±0.2°, 13.3±0.2° and 21.1±0.2° in an X-ray powder diffraction. Eutectic form A has a high purity, a good light radiation stability, a high temperature stability, a high humidity stability and an accelerated stability, is easy to store, and has a slow moisture absorption under the condition of relatively low humidity, wherein the weight gain of eutectic form A by moisture absorption is not more than 1.08% when the relative humidity increases from 0 to 60% RH. Production conditions for eutectic form A are easy to control, same has a simple preparation process and a stable quality, and is easy to industrially produce on a large-scale.

18 Claims, 15 Drawing Sheets

EUTECTIC FORM A OF ELAGOLIX AND PYRIMETHAMINE, PREPARATION METHOD THEREFOR AND USE THEREOF

CROSS-REFERENCE TO RELATED APPLICATIONS

This application is a continuation of International Application No. PCT/CN2019/098642, filed Jul. 31, 2019, designating the United States, the entire contents of which are incorporated herein by reference.

TECHNICAL FIELD

The present disclosure relates to the technical field of pharmaceutical crystals, in particular to a eutectic form A of Elagolix and pyrimethamine, and a preparation method and use thereof.

BACKGROUND

3-[2(R)-{hydroxycarbonylpropyl-amino}-2-phenethyl]-5-(2-fluoro-3-methoxyphenyl)-1-[2-fluoro-6-(trifluoromethyl)benzyl]-6-methyl-pyrimidine-2,4(1H,3H)-dione of a formula (I), also known as Elagolix, is an oral gonadotropin releasing hormone (GnRH) receptor antagonist, competitively binds to a GnRH receptor in the pituitary gland to block a GnRH signaling pathway, so as to reversibly reduce the secretion of ovarian sex hormones, estradiol and progesterone, is jointly developed by AbbVie and Neurocrine biosciences, was approved by the U.S. Food and Drug Administration on Jul. 23, 2018 for the treatment of pains caused by endometriosis, and became a first new oral drug for such indications in more than 10 years.

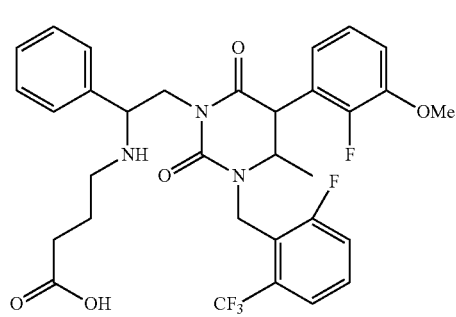

(I)

At present, Elagolix produced and sold at home and abroad exists in the form of sodium salt, and is prepared according to a method in Example 1 of Chinese issued patent document CN100424078B, however, the inventors have found that the obtained Elagolix sodium is unstable when stored under high temperature, high humidity and light conditions, is easily hygroscopic, and exhibits high hygroscopicity under low humidity conditions of 20-60% RH, and thus is difficult to be used as a pharmaceutical raw material, requires strict management during use, and is not suitable for use as a pharmaceutical raw material.

SUMMARY

Therefore, the technical problem to be solved by the present disclosure is to solve the problems of poor stability of the existing GnRH receptor antagonist-Elagolix sodium and easy hygroscopicity under low humidity conditions.

In order to achieve the above object, the present inventors have conducted a careful study and found that the Elagolix sodium prepared in Example 1 of the above patent document is amorphous, and found that it is difficult to prepare crystal-form powder from both an Elagolix free acid and the Elagolix sodium. Then, through in-depth study of an eutectic of Elagolix, the inventors found that an eutectic form A of Elagolix and pyrimethamine has excellent stability and good hygroscopicity, thus completing the present disclosure.

In particular, the present disclosure relates to the following technical solutions.

The present disclosure provides an eutectic form A of Elagolix and pyrimethamine, wherein an X-ray powder diffraction of the eutectic form A using Cu-Kα radiation has characteristic peaks at 2θ angles of 8.1±0.2°, 12.2±0.2°, 13.3±0.2° and 21.1±0.2°.

Further, the X-ray powder diffraction of the eutectic form A using Cu-Kα radiation also has a characteristic peak at 2θ angle of 24.4±0.2°.

Further, the X-ray powder diffraction of the eutectic form A using Cu-Kα radiation also has characteristic peaks at 2θ angles of 16.2±0.2° and 22.0±0.2°.

Further, the X-ray powder diffraction of the eutectic form A using Cu-Kα radiation also has characteristic peaks at 2θ angles of 28.1±0.2° and 31.7±0.2°.

Further, the eutectic form A has following characteristic peaks in its X-ray powder diffraction pattern:

| 2θ (±0.2°) | d (Å) | I % |
|---|---|---|
| 8.074 | 10.9408 | 9.6 |
| 12.176 | 7.2631 | 7 |
| 13.26 | 6.6715 | 37.3 |
| 21.138 | 4.1996 | 47.3 |
| 22.017 | 4.0338 | 4.1 |
| 24.44 | 3.6392 | 86.4 |
| 31.699 | 2.8204 | 100 |

Further, the eutectic form A has following characteristic peaks in its X-ray powder diffraction pattern:

| 2θ (±0.2°) | d (Å) | I % |
|---|---|---|
| 8.074 | 10.9408 | 9.6 |
| 12.176 | 7.2631 | 7 |
| 13.26 | 6.6715 | 37.3 |
| 15.838 | 5.5909 | 8 |
| 16.157 | 5.4813 | 9.3 |
| 21.138 | 4.1996 | 47.3 |
| 22.017 | 4.0338 | 4.1 |
| 23.9 | 3.72 | 11.3 |
| 24.44 | 3.6392 | 86.4 |
| 26.58 | 3.3508 | 24 |
| 27.361 | 3.2569 | 8.9 |
| 28.08 | 3.1752 | 20.5 |
| 31.699 | 2.8204 | 100 |
| 32.163 | 2.7807 | 14.4 |
| 33.143 | 2.7007 | 5.1 |
| 34.539 | 2.5947 | 8.6 |
| 37.223 | 2.4136 | 8.6 |
| 42.52 | 2.1243 | 5.5 |

Further, the eutectic form A has an X-ray powder diffraction pattern substantially as shown in FIG. 7-A.

Further, a differential scanning calorimetry curve of the eutectic form A has two endothermic peaks, wherein a first endothermic peak is at a temperature of 69.49±2° C., and a second endothermic peak is at a temperature of 204.78±2° C.

Further, the eutectic form A has a differential scanning calorimetry curve substantially as shown in FIG. 8.

Further, in a thermo gravimetric analysis curve of the eutectic form A has a thermal weight loss of less than 6.2% before 193° C.

Further, the eutectic form A has a thermo gravimetric analysis curve substantially as shown in FIG. 9.

The present disclosure further provides a preparation method for the eutectic form A as described in any one of the above, including the steps of: dissolving a raw drug of Elagolix sodium in an organic solvent, adding a concentrated hydrochloric acid thereto, adding an aqueous solution of pyrimethamine, stirring, filtering and drying to obtain an eutectic.

Further, a molar ratio of the raw drug of Elagolix sodium to pyrimethamine is in a range of from 1.0:1.1 to 1.0:1.5.

The present disclosure further provides a pharmaceutical composition, including the eutectic form A as described in any one of the above, and a pharmaceutically acceptable excipient.

The present disclosure further provides use of a pharmaceutically effective amount of the eutectic form A as described in any one of the above, or the eutectic form A prepared by the preparation method above, or the pharmaceutical composition for the manufacture of a medicament for the treatment of a sex hormone-related disease state, a gonadotropin releasing hormone-related disease state, infertility, lupus erythematosus, irritable bowel syndrome, premenstrual syndrome, hirsutism, short stature or sleep disorder in an individual.

Further, the sex hormone-related disease state is cancer, benign prostatic hypertrophy or uterine fibroids; wherein preferably, the cancer is prostate cancer, uterine cancer, breast cancer or pituitary gonadotropic cell adenoma.

Further, the sex hormone-related disease state is endometriosis, polycystic ovary disease, uterine leiomyoma or precocious puberty.

The present disclosure further provides a method for treating a sex hormone-related disease state, a gonadotropin releasing hormone-related disease state, infertility, lupus erythematosus, irritable bowel syndrome, premenstrual syndrome, hirsutism, short stature or sleep disorder in an individual, including the step of administering a pharmaceutically effective dose of the above pharmaceutical composition to a patient.

The present disclosure further provides a method for treating cancer, benign prostatic hypertrophy, uterine fibroids, endometriosis, polycystic ovary disease, uterine leiomyoma or precocious puberty, including the step of administering a pharmaceutically effective dose of the above pharmaceutical composition to a patient.

Further, the cancer is prostate cancer, uterine cancer, breast cancer, or pituitary gonadotropic cell adenoma.

The technical solutions of the present disclosure have the following advantages:

the eutectic form A of Elagolix and pyrimethamine provided by the present disclosure has high purity, good light stability, high temperature stability, high humidity stability and accelerated stability, and has a melting point of 204° C., the hygroscopic weight gain of the eutectic form A is not higher than 1.08% when the relative humidity rises from 0 to 60% RH, the eutectic form A is slowly hygroscopic under the condition of relatively low humidity, the production conditions is convenient to control, the preparation process is simple, the quality is stable, and large-scale industrial production is easy.

BRIEF DESCRIPTION OF THE DRAWINGS

In order to more clearly illustrate the specific embodiments of the present disclosure or the technical solutions in the prior art, the accompanying drawings, which need to be used in the description of the specific embodiments or the prior art, will be briefly described below. Obviously, the drawings in the following description are some embodiments of the present disclosure, and other drawings may be obtained from these drawings by those of ordinary skill in the art without creative labor.

DETAILED DESCRIPTION OF THE EMBODIMENTS

Figure 1:
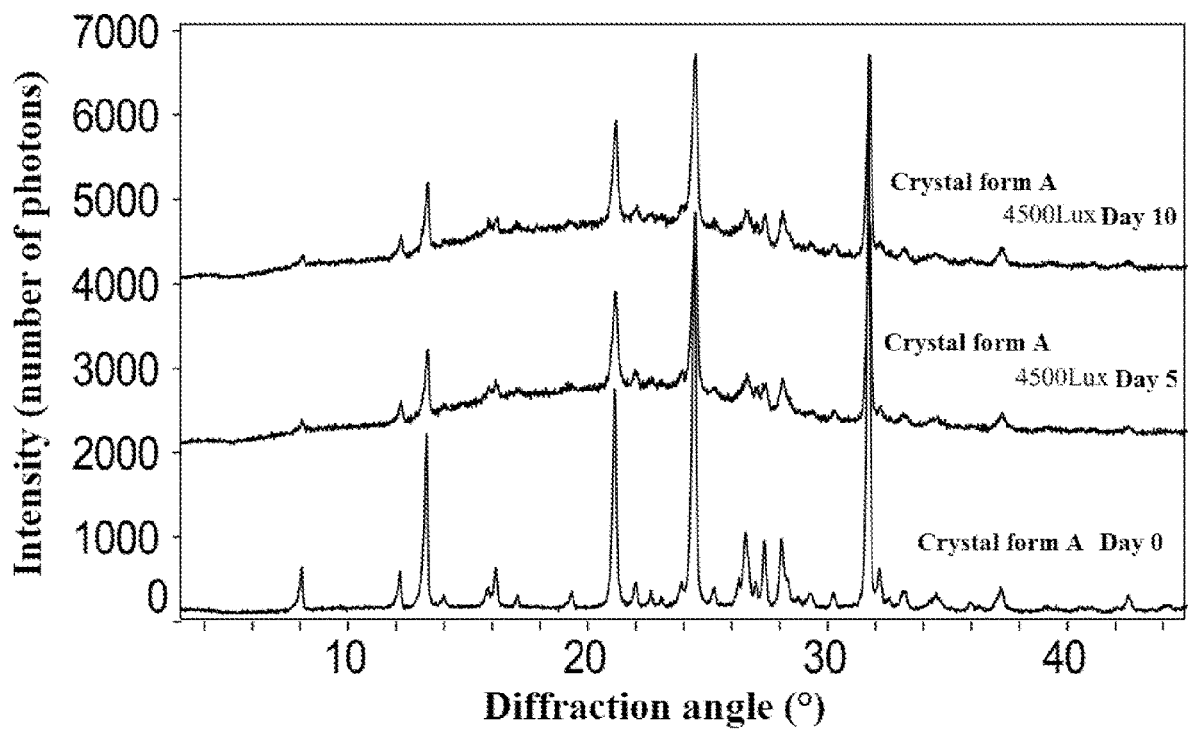
FIG. 1 is a comparative XRPD pattern showing light stability of an eutectic form A in Experimental example 1 of the present disclosure.
Figure 2:
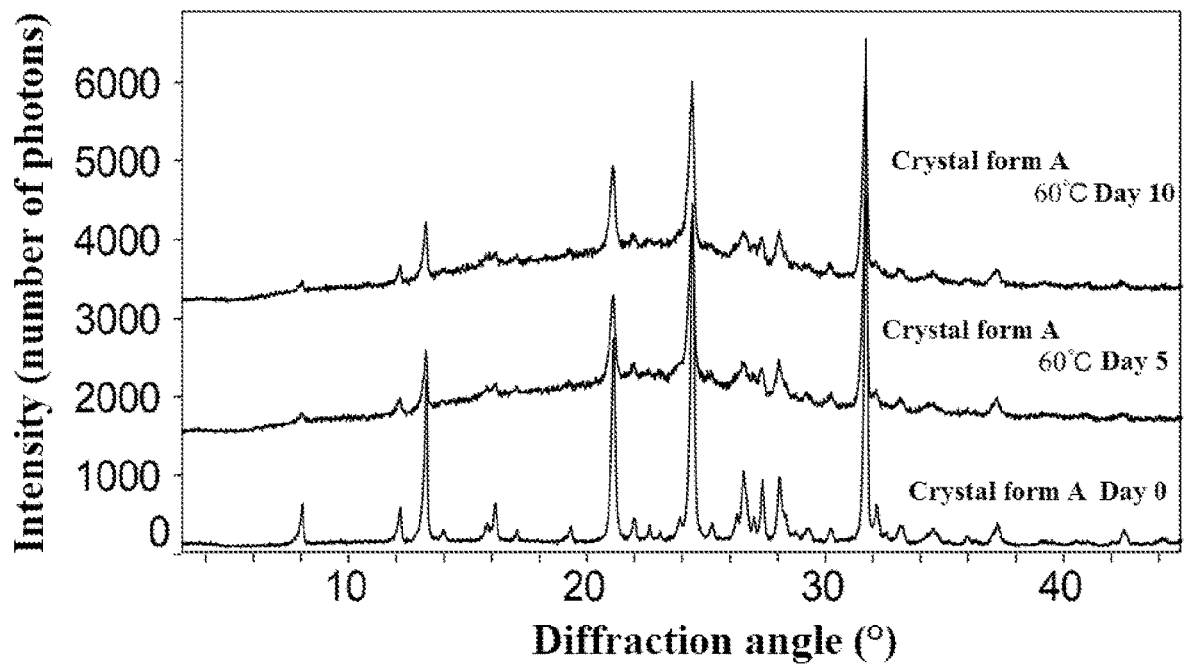
FIG. 2 is a comparative XRPD pattern showing high temperature stability of the eutectic form A in Experimental example 1 of the present disclosure.
Figure 3:
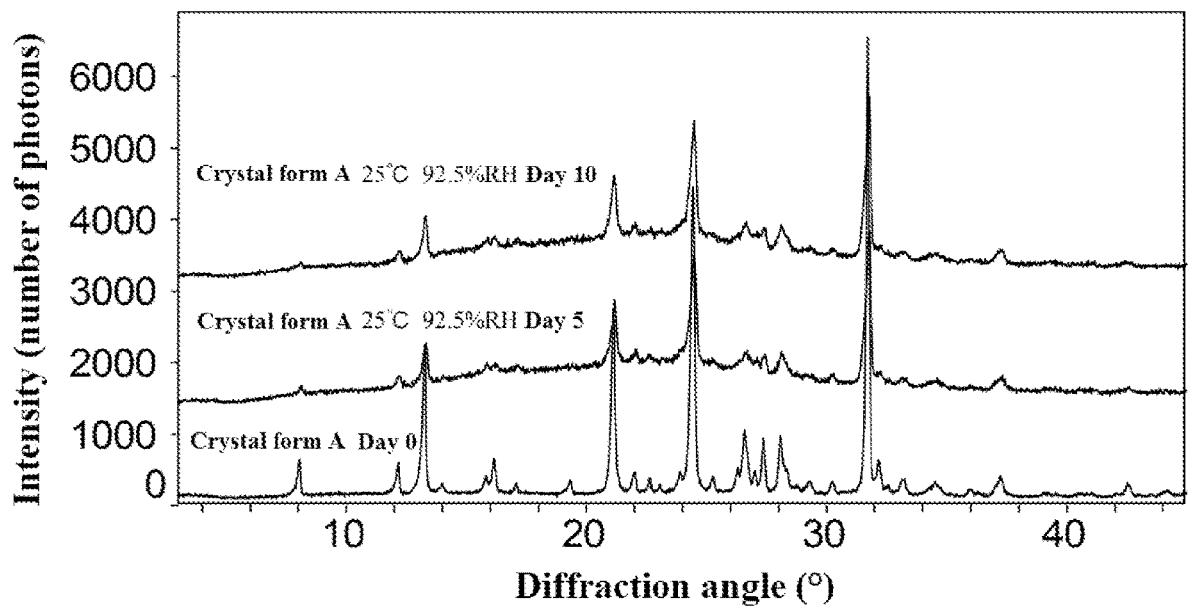
FIG. 3 is a comparative XRPD pattern showing high humidity stability of the eutectic form A in Experimental example 1 of the present disclosure.
Figure 4:
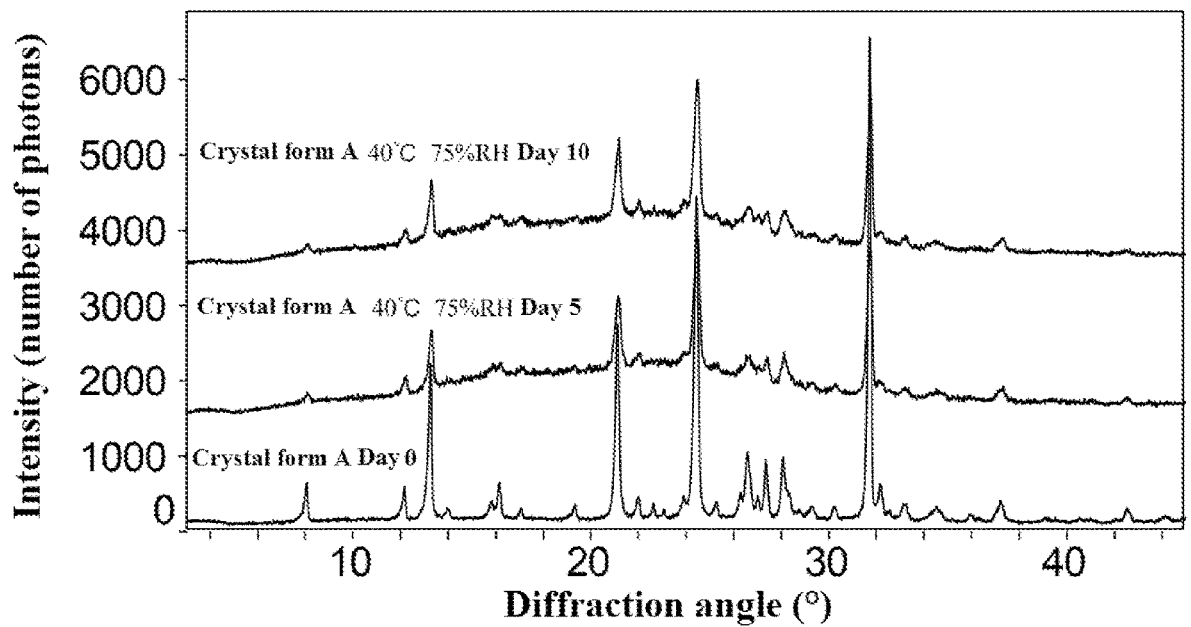
FIG. 4 is a comparative XRPD pattern showing accelerated stability of the eutectic form A in Experimental example 1 of the present disclosure.

In the description and claims of this application, the compounds are named according to a chemical structural formula. If a name of the compound is inconsistent with the chemical structural formula when a same compound is represented, the compound is named based on the chemical structural formula or a chemical reaction formula.

In this application, unless otherwise indicated, scientific and technical terms used herein have the meanings commonly understood by those skilled in the art. However, for a better understanding of the present disclosure, definitions and explanations of some of the related terms are provided below. In addition, when definitions and explanations of the terms provided in this application are inconsistent with the meaning generally understood by those skilled in the art, the meanings of the terms are based on the definitions and explanations of the terms provided in this application.

X-ray powder diffraction (XRPD) refers to that when a beam of X-ray irradiates on an object, the X-ray is scattered by atoms in the object, and each atom produces scattered waves. These waves interfere with each other, resulting in diffraction. As a result of the superposition of diffracted waves, the intensity of the rays is strengthened in some directions and weakened in other directions. A crystal structure can be obtained by analyzing the diffraction results. An X-ray diffractometer is to use a diffraction principle to accurately determine the crystal structure, texture and stress of a substance, and accurately carry out phase analysis, qualitative analysis and quantitative analysis. For a crystalline material, when a crystal to be measured is at different angles to an incident beam, those crystal planes satisfying Bragg diffraction will be detected, which are reflected in the XRPD pattern with diffraction peaks having different diffraction intensities. For an amorphous material, there are some diffuse scattering peaks in the XRPD pattern of the amorphous material because there is no long-range order of atomic arrangement in the crystal structure, but only a short-range order in the range of several atoms.

The "2θ angle" of the present disclosure means that X-ray diffraction analysis is based on a Bragg formula (the Bragg formula is $2d \sin\theta = n\lambda$), wherein "θ" refers to a grazing angle or Bragg angle, and is a complementary angle of an incident angle, and "2θ" refers to a diffraction angle; "d" refers to an interplanar spacing of two adjacent crystal planes in a crystal lattice, in Angstroms (Å); "λ" refers to a wavelength of X-rays; and "n" is any positive integer, and the X-ray diffraction is referred to as n-order diffraction accordingly. In the XRPD pattern, the abscissa corresponding to the powder diffraction peak is a 2θ angle, and an error range of the 2θ angle at the peak position is ±0.3°, preferably ±0.2°. When the crystal form of the present disclosure are determined by X-diffraction, sometimes there will be a slight measurement error for the measured peaks due to the measurement instrument or measurement conditions, so this error should be taken into account when determining the crystal structure. Therefore, the applicant considers the error range (±0.2) when determining the 2θ angle. "Substantially as shown in the figure" means that at least 50%, or at least 60%, or at least 70%, or at least 80%, or at least 90%, or at least 99% of the peaks in the pattern are shown in the figure.

Differential scanning calorimetry (DSC) is a thermal analysis method. The difference in power (e.g., in the form of heat) input to a sample and a reference is measured as a function of temperature at a programmed temperature. A curve recorded by a differential scanning calorimeter is called a DSC curve, using a heat absorption rate or heat release rate of a sample, namely a heat flow rate dH/dt (unit: mJ/s) or heat flow (unit: W/g) as an ordinate, and the temperature T or time t as an abscissa, and various thermodynamic and kinetic parameters, such as specific heat capacity, reaction heat, transformation heat, phase diagram, reaction rate, crystallization rate, polymer crystallinity, sample purity, etc., can be measured.

Thermo gravimetric analysis (TGA) is a thermal analysis technique that measures the mass of a sample to be measured as a function of temperature at a programmed temperature, and is used to study the thermal stability and composition of substances. A thermogravimetric method is to measure the mass of a substance as a function of the temperature (or time) under programmed temperature control. When the measured substance sublimates, vaporizes, decomposes into gas or loses crystal water during the heating process, the mass of the measured substance will change. At this time, the thermogravimetric curve is not a straight line but decreases somewhat. By analyzing the thermogravimetric curve, it is possible to know at what degrees the measured substance changes, and according to the weight loss, it is possible to calculate how much material, such as crystal water, has been lost. The TGA experiment is helpful to study the changes of crystal properties, such as the physical phenomena of substances such as melting, evaporation, sublimation and adsorption, and is also helpful to study the chemical phenomena of substances such as dissociation, oxidation, reduction, thermal stability, decomposition process, quantitative analysis of components, influence of additives and fillers, moisture and volatiles, reaction kinetics, etc. Thermo gravimetric analysis can generally be divided into two categories: dynamic (temperature rise) and static (constant temperature). The curve obtained by the thermogravimetric test is called the thermogravimetric curve (a TG curve), and the TG curve takes the mass as the ordinate, which can also be expressed in other forms such as weight loss percentage; the temperature (or time) is used as the abscissa, and the increase in temperature (or time) is indicated from left to right.

Experimental Scheme

The following examples are provided for a better further understanding of the present disclosure, are not limited to the preferred embodiments described, and do not limit the content and protection scope of the present disclosure. Any product that is the same or similar to the present disclosure, obtained by anyone under the Enlightenment of the present disclosure or by combining the present disclosure with the features of other prior art, fall within the protection scope of the present disclosure.

A raw material of a raw drug of Elagolix sodium used in the following Experimental examples 1 and 2, Example 1 and Comparative Examples 2-23 of the present disclosure is prepared in Comparative Example 1. A raw material of an Elagolix free acid used in Comparative Example 1 below is commercially available or prepared according to the methods reported in the literature, such as the literature CN100424078B.

Experimental Example 1 Test on the Stability of an Eutectic Form a

1. Experimental Method

Light stability: samples of a raw drug of Elagolix sodium and an eutectic form A formed by Elagolix and pyrimethamine (prepared in Comparative example 1 and Example 1, respectively) were taken and separately placed at 25° C. under light conditions of 4500 Lux for 30 days, sampling was conducted at fixed time points on day 5, day 10 and day 30, respectively to determine the XRPD pattern of the eutectic form A, and the content of Elagolix in the raw drug of Elagolix sodium and the eutectic form A, and the determined XRPD pattern of the eutectic form A, and the determined content of Elagolix in the raw drug of Elagolix sodium and the eutectic form A were compared with those on day 0.

High temperature stability: samples of a raw drug of Elagolix sodium and an eutectic form A formed by Elagolix and pyrimethamine (prepared in Comparative example 1 and Example 1, respectively) were taken and separately placed at 60° C. for 30 days, sampling was conducted at fixed time points on day 5, day 10 and day 30, respectively to determine the XRPD pattern of the eutectic form A, and the content of the raw drug of Elagolix sodium and the eutectic form A, and the determined XRPD pattern of the eutectic form A, and the determined content of the raw drug of Elagolix sodium and the eutectic form A were compared with those on day 0.

High humidity stability: samples of a raw drug of Elagolix sodium and an eutectic form A formed by Elagolix and pyrimethamine (prepared in Comparative example 1 and Example 1, respectively) were taken and separately placed at 25° C. at 92.5% RH for 30 days, sampling was conducted at fixed time points on day 5, day 10 and day 30, respectively to determine the XRPD pattern of the eutectic form A, and the content of the raw drug of Elagolix sodium and the eutectic form A, and the determined XRPD pattern of the eutectic form A, and the determined content of the raw drug of Elagolix sodium and the eutectic form A were compared with those on day 0.

Accelerated stability: samples of a raw drug of Elagolix sodium and an eutectic form A formed by Elagolix and pyrimethamine (prepared in Comparative example 1 and Example 1, respectively) were taken and separately placed at 40° C. at 75% RH for 30 days, sampling was conducted at fixed time points on day 5, day 10 and day 30, respectively to determine the XRPD pattern of the eutectic form A, and the content of the raw drug of Elagolix sodium and the eutectic form A, and the determined XRPD pattern of the eutectic form A, and the determined content of the raw drug of Elagolix sodium and the eutectic form A were compared with those on day 0.

The specific stability test method can refer to the method in Appendix XIC of Part II of Chinese Pharmacopoeia (2015 Edition); and the purity was detected by an HPLC method, and can be determined by an external standard method with reference to the method in Appendix VD of Chinese Pharmacopoeia (2015 Edition) by using the sample on day 0 as a control.

Operating Conditions for HPLC

Instrument: high performance liquid chromatograph (model: Agilent Technologies 1260)

Chromatographic column: shiseido CAPCELL PAK C18 column (5 μm, 250 mm×4.6 mm)

Mobile Phase Composition and Gradient Elution Procedure:

TABLE 1

Gradient elution procedure table

| Time (min) | 0.1% phosphoric acid aqueous solution (%) | Acetonitrile (%) |
|---|---|---|
| 0 | 95 | 5 |
| 5 | 5 | 95 |
| 6 | 95 | 5 |
| 10 | 95 | 5 |

Detection wavelength: 254 nm

Flow rate: 1 mL/min

Injection volume: 10 μL

Column temperature: 30° C.

2. Experimental Results

It can be seen from FIGS. 1-4 that the stability of the eutectic form A was good under the conditions of high light (25° C., 4500 Lux), high temperature (60° C.), high humidity (25° C., 92.5% RH) and accelerated (40° C., 75% RH), and no crystal transformation occurred.

From Tables 2 and 3, it can be seen that the relative purity of the raw drug of Elagolix sodium was significantly reduced under the conditions of high temperature (60° C.), high humidity (25° C., 92.5% RH) and accelerated (40° C., 75% RH), and the stability was poor. In particular, the purity decreased more than 4% under high humidity and accelerated conditions, while the relative purity of the eutectic form A remained unchanged (the change of purity was less than 1.5%) under the conditions of high light (25° C., 4500 Lux), high temperature (60° C.), accelerated (40° C., 75% RH) and high humidity (25° C., 92.5% RH), and the stability of the eutectic form A was good.

TABLE 2

Stability test results of the raw drug of Elagolix sodium

| Condition | Starting purity (day 0) | Purity after 1 month | Change in purity |
|---|---|---|---|
| 25° C., 4500 Lux | 98.41% | 97.12% | 1.29% |
| 60° C. | | 95.23% | 3.18% |
| 40° C., 75% RH | | 94.13% | 4.28% |
| 25° C., 92.5% RH | | 93.78% | 4.63% |

TABLE 3

Stability test results of the eutectic form A

| Condition | Starting purity (day 0) | Purity after 1 month | Change in purity |
|---|---|---|---|
| 25° C., 4500 Lux | 98.4% | 98.13% | 0.27% |
| 60° C. | | 97.87% | 0.53% |
| 40° C., 75% RH | | 97.05% | 1.35% |
| 25° C., 92.5% RH | | 97.27% | 1.13% |

Experimental Example 2 Water Adsorption Experiment

Figure 5:
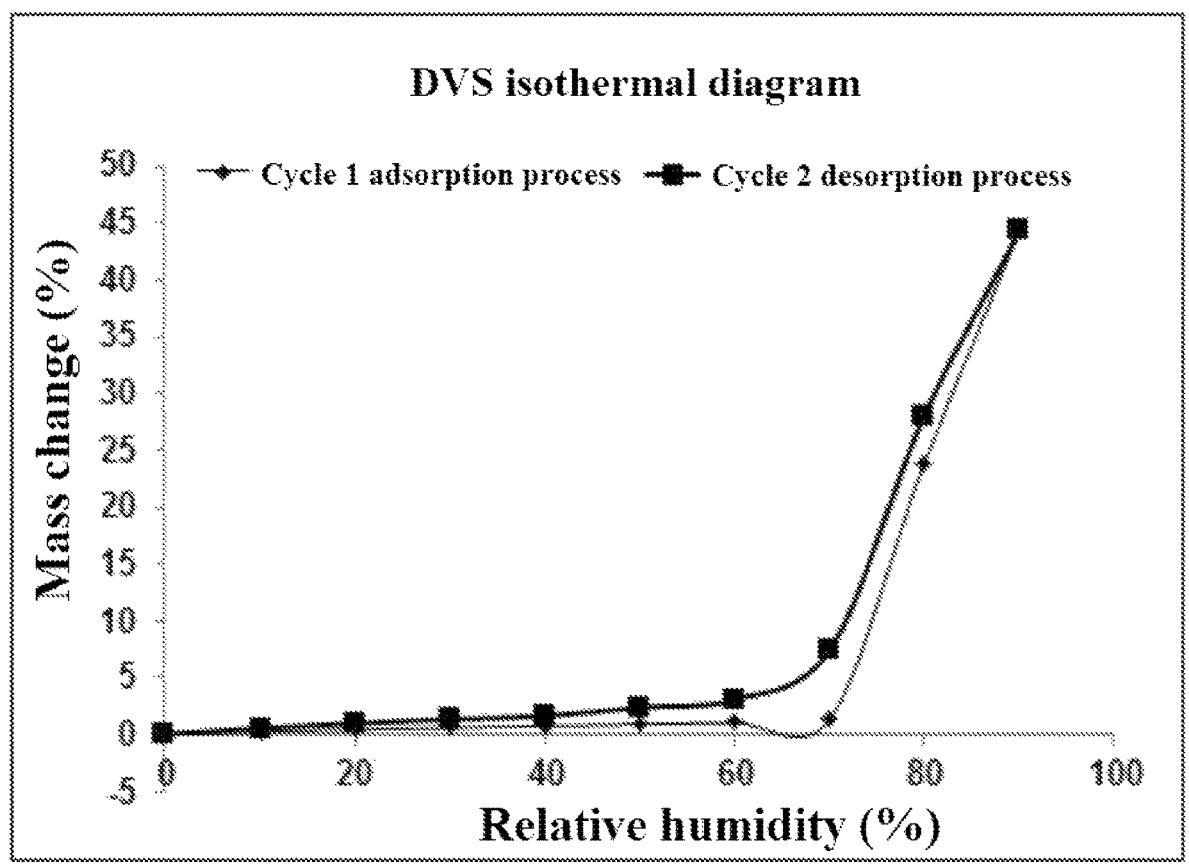
FIG. 5 is a DVS curve of an eutectic form A in Experimental example 2 of the present disclosure.

Samples of a raw drug of Elagolix sodium and an eutectic form A formed by Elagolix and pyrimethamine (prepared in Comparative example 1 and Example 1, respectively) were taken and separately subjected to water adsorption experiments. The experimental instrument was DVS intrinsic of SMS Company, UK, and the experimental condition was 25° C. The relative humidity gradually increased from 0 to 90% RH at a 10% humidity change step, and the constant equilibrium time of each humidity was 10 min. The results are shown in FIGS. 5-6.

Figure 6:
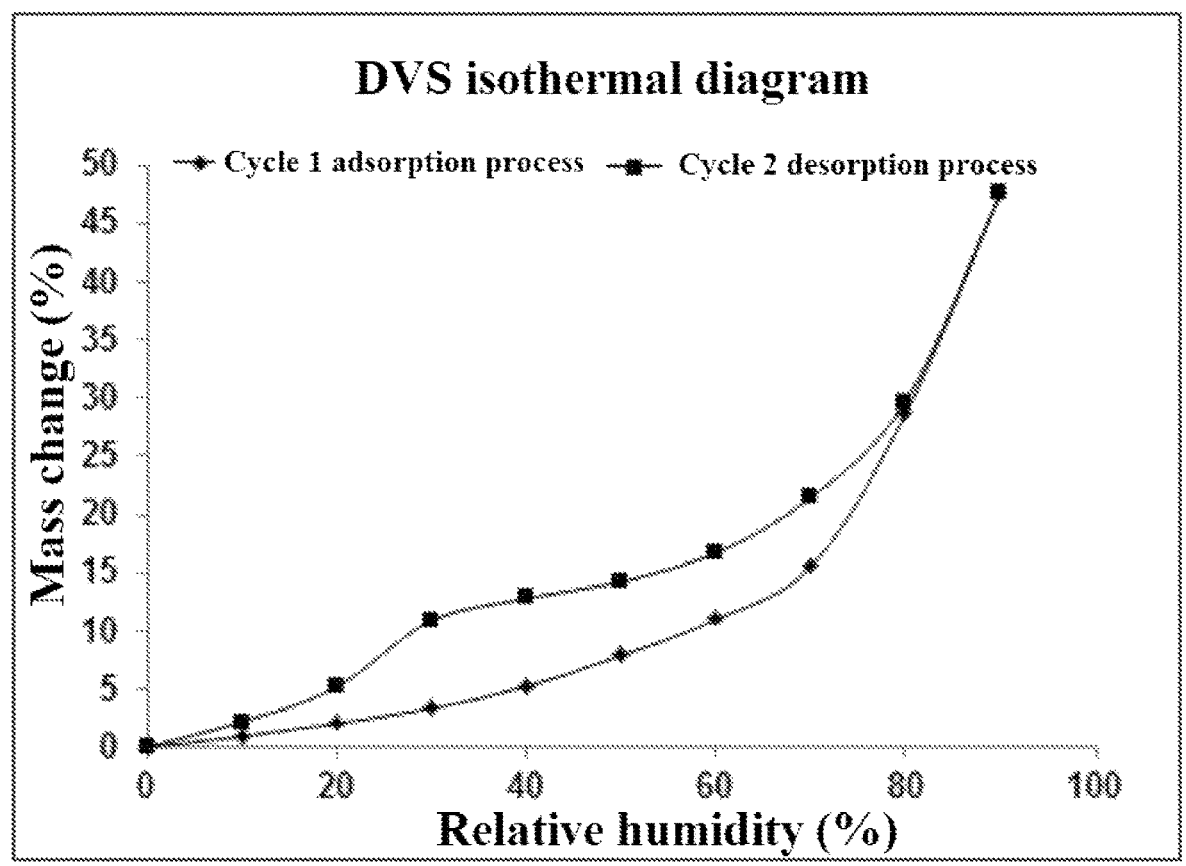
FIG. 6 is a DVS curve of a raw drug of Elagolix sodium in Experimental example 2 of the present disclosure.
Figure 7:
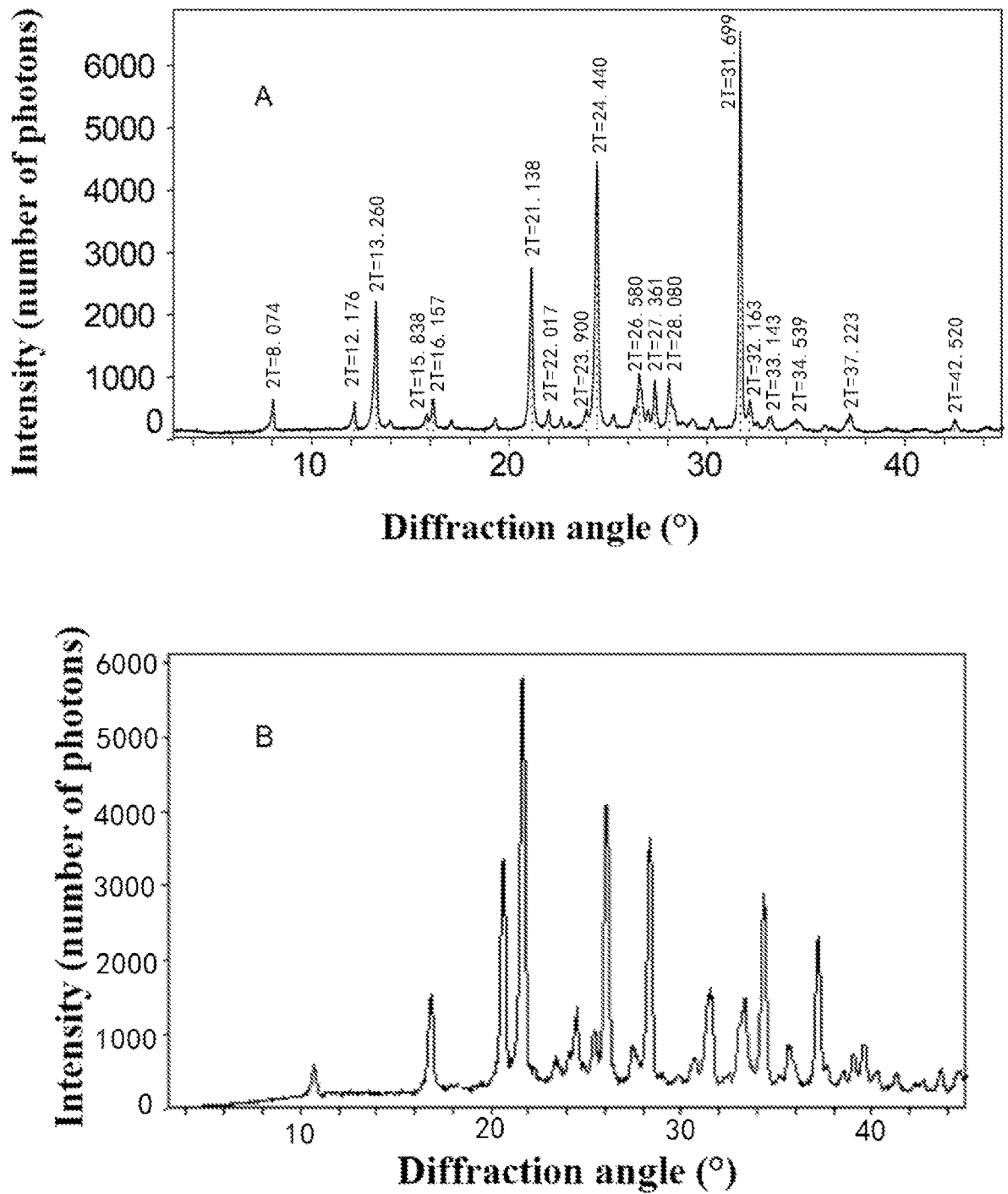
FIG. 7 is X-ray diffraction patterns of pyrimethamine and an eutectic form A in Example 1 of the present disclosure, wherein A is the X-ray diffraction pattern of the eutectic form A; B is the X-ray diffraction pattern of pyrimethamine.

The hygroscopic weight gain of the eutectic form A is less than 1.08% when the humidity was 60%, as shown in FIG. 6, while the hygroscopic weight gain of the raw drug of Elagolix sodium is less than 11.01% when the humidity was 60%, as shown in FIG. 7, indicating that the eutectic form A has excellent resistance to hygroscopicity under the condition of low humidity (60% RH or below) compared with the raw drug of Elagolix sodium, which is conducive to the transportation and storage of drugs.

In conclusion, the eutectic form A formed by Elagolix and pyrimethamine provided in this application has good light stability, high temperature stability, high humidity stability, and is not easily hygroscopic under low humidity conditions of 60% RH. However, the light stability, high temperature stability and high humidity stability of the raw drug of Elagolix sodium are not good, and the raw drug of Elagolix sodium is easily hygroscopic under low humidity conditions.

Example 1 Preparation of Eutectic Form a 14.3 mg of pyrimethamine was weighed, and 0.2 ml of water was added to obtain a pyrimethamine aqueous solution for later use. 33.0 mg of a raw drug of Elagolix sodium was weighed, 1.2 ml of ethanol, 5.5 µl of concentrated hydrochloric acid, and the above pyrimethamine aqueous solution were added, the obtained mixture was stirred for 12 h, and filtered to obtain a solid, and the obtained solid was dried under vacuum at room temperature to obtain a white solid. XRPD test showed that the white solid was an eutectic form A. The structure of the eutectic form A was characterized by nuclear magnetic resonance ($^1$H-NMR), differential scanning calorimetry (DSC) and thermo gravimetric analysis (TGA), respectively, thereby further confirming the formation of the eutectic form A.

① X-Ray Powder Diffraction (XRPD)

X-ray powder diffraction was performed by using the eutectic form A and pyrimethamine, respectively under the following test conditions:

Determination was performed by using Cu-Kα under a voltage of 40 KV, and a current of 40 mA at a test angle of 3-45°, a step length of 0.02°, and a light tube slit width of 2 mm by using a Dtex detector, and a Japanese Rigaku Uitima IV type X-ray powder diffractometer.

The XRPD pattern of the above eutectic form A is shown in FIG. 7-A, and an X-ray powder diffraction of the eutectic form A using Cu-Kα radiation has characteristic peaks at 2θ angles of 8.1±0.2°, 12.2±0.2°, 13.3±0.2° and 21.1±0.2°, also has a characteristic peak at 2θ angle of 24.4±0.2°, also has characteristic peaks at 2θ angles of 16.16±0.2° and 22.02±0.2°, and also has characteristic peaks at 2θ angles of 28.08±0.2°, 31.70±0.2° and 32.16±0.2°. The specific X-ray diffraction positions of the eutectic form A are shown in Table 4. Combined with the XRPD pattern of pyrimethamine (7-B), it can be known that the product is an eutectic form of a raw drug of Elagolix sodium and pyrimethamine.

TABLE 4

X-ray diffraction results table of eutectic form A

| 2-Theta | d (Å) | I % |
|---|---|---|
| 11.733 | 7.5359 | 12.3 |
| 17.539 | 5.0523 | 17.5 |
| 18.08 | 4.9024 | 53.1 |
| 19.739 | 4.4938 | 19.1 |
| 23.546 | 3.7752 | 6 |
| 25.262 | 3.5226 | 30.8 |
| 27.355 | 3.2576 | 10 |
| 28.264 | 3.1548 | 19.8 |
| 28.502 | 3.1291 | 32.7 |
| 29.197 | 3.0561 | 42 |
| 31.661 | 2.8237 | 100 |
| 32.596 | 2.7448 | 12 |
| 32.919 | 2.7186 | 8.8 |
| 34.162 | 2.6225 | 9.8 |
| 35.6 | 2.5198 | 12.4 |
| 36.719 | 2.4455 | 9.3 |
| 39.078 | 2.3032 | 9.6 |
| 40.705 | 2.2148 | 4.3 |
| 42.54 | 2.1234 | 7 |
| 43.019 | 2.1008 | 6.8 |

② DSC Determination

DSC determination was performed by using the eutectic form A under the following conditions:

Determination was performed by a Q2000 differential scanning calorimeter of TA Instruments Inc, USA, with nitrogen protection and a heating rate of 10° C./min.

Figure 8:
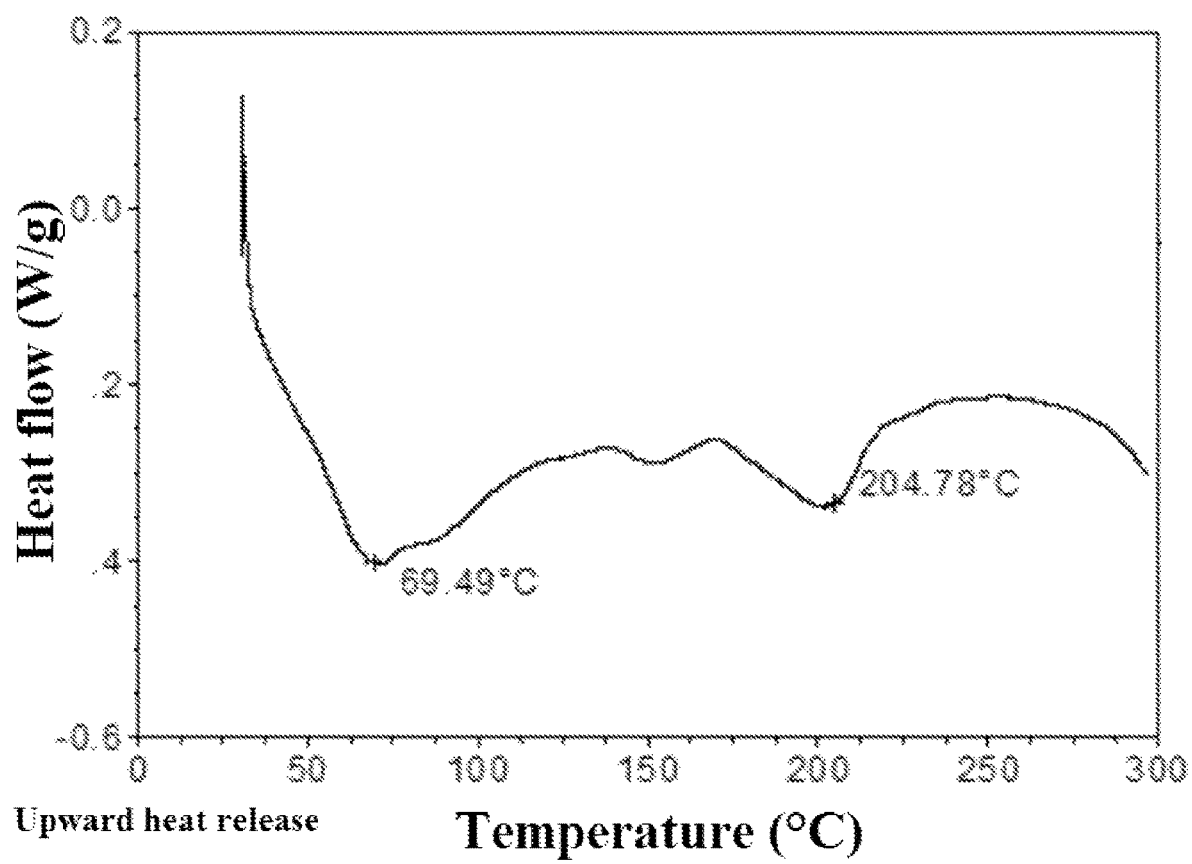
FIG. 8 is a DSC curve of the eutectic form A in Example 1 of the present disclosure.

The DSC pattern of the eutectic form A is shown in FIG. 8. The DSC pattern of the eutectic form A has two endothermic peaks, and a second endothermic peak is due to melting of the eutectic form A. The peak temperature of a first endothermic peak is 69.5° C., and the peak temperature of the second endothermic peak is 204.8° C.

③ TGA Detection

TGA determination was performed by using the eutectic form A under the following conditions:

Determination was performed by Q500 of TA Instruments Inc, USA, and the test conditions were as follows: a heating rate was 10° C./min.

Figure 9:
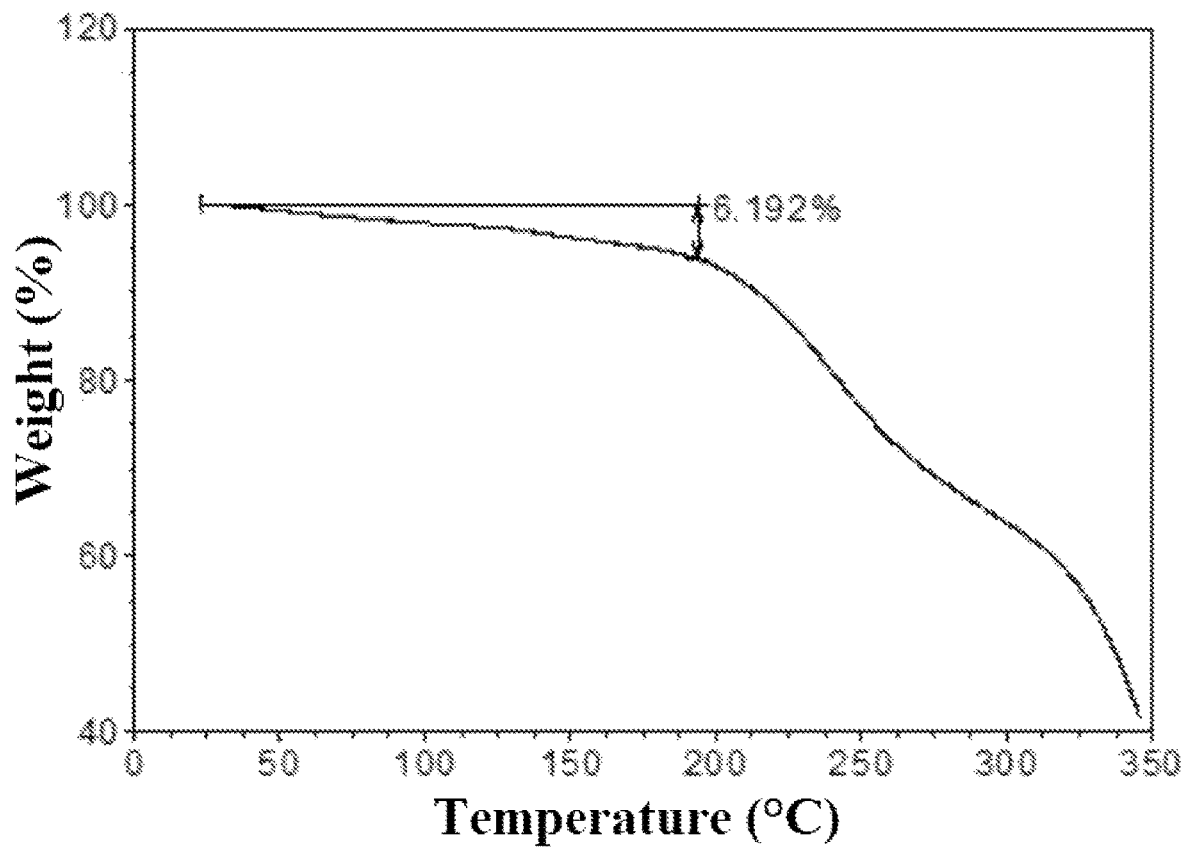
FIG. 9 is a TGA curve of the eutectic form A in Example 1 of the present disclosure.

The TGA pattern of the eutectic form A is shown in FIG. 9, and 6.2% of the eutectic form A was desolventized at 193° C.

④ $^1$H-NMR Detection $^1$H-NMR detection was performed by using pyrimethamine and the eutectic form A, respectively under the following test conditions:

BRUKER AM-400 nuclear magnetic resonance spectrometer, solvent: DMSO-$d_6$.

Figure 10:
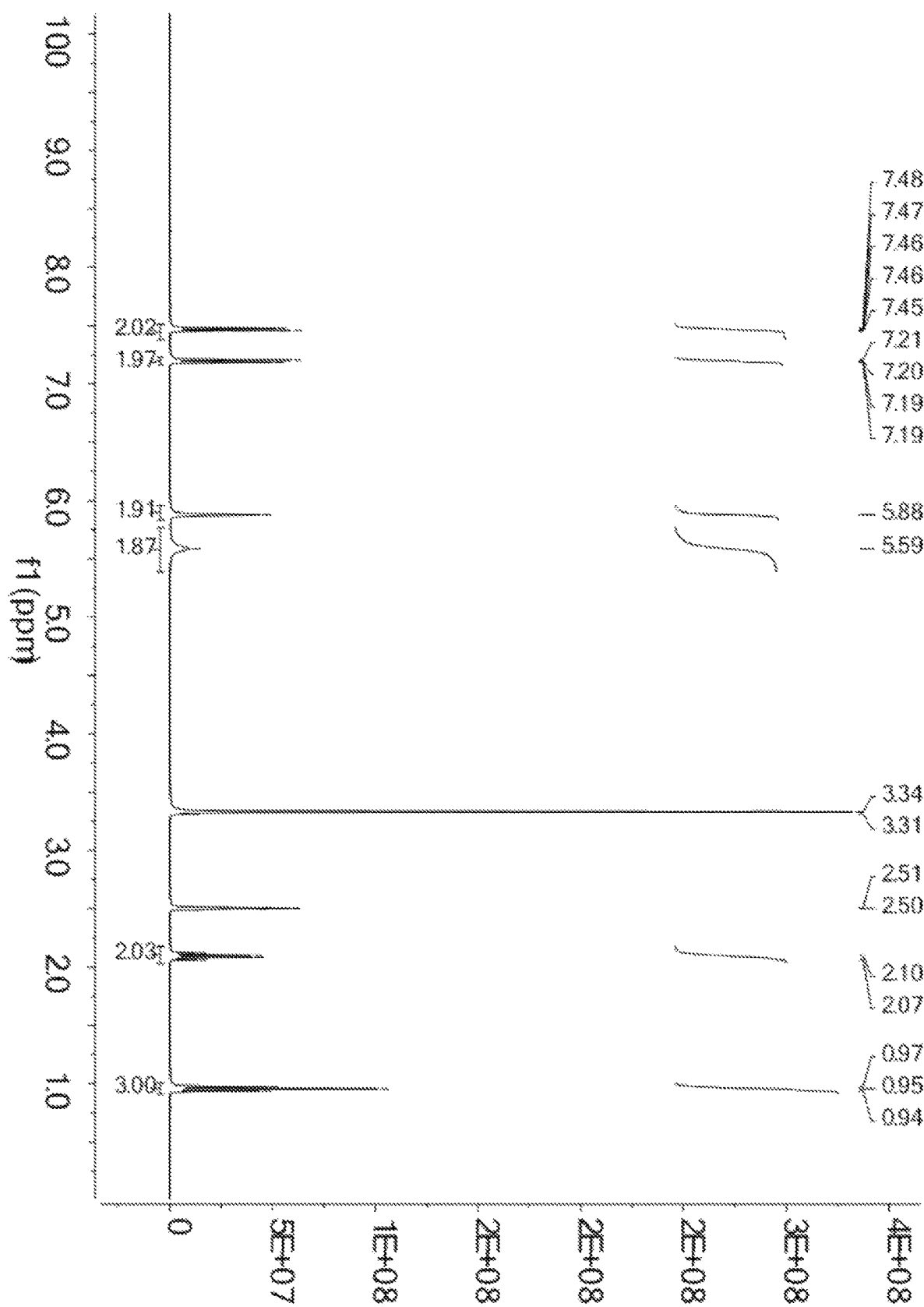
FIG. 10 is a $^1$H-NMR spectrum of pyrimethamine in Example 1 of the present disclosure.
Figure 11:
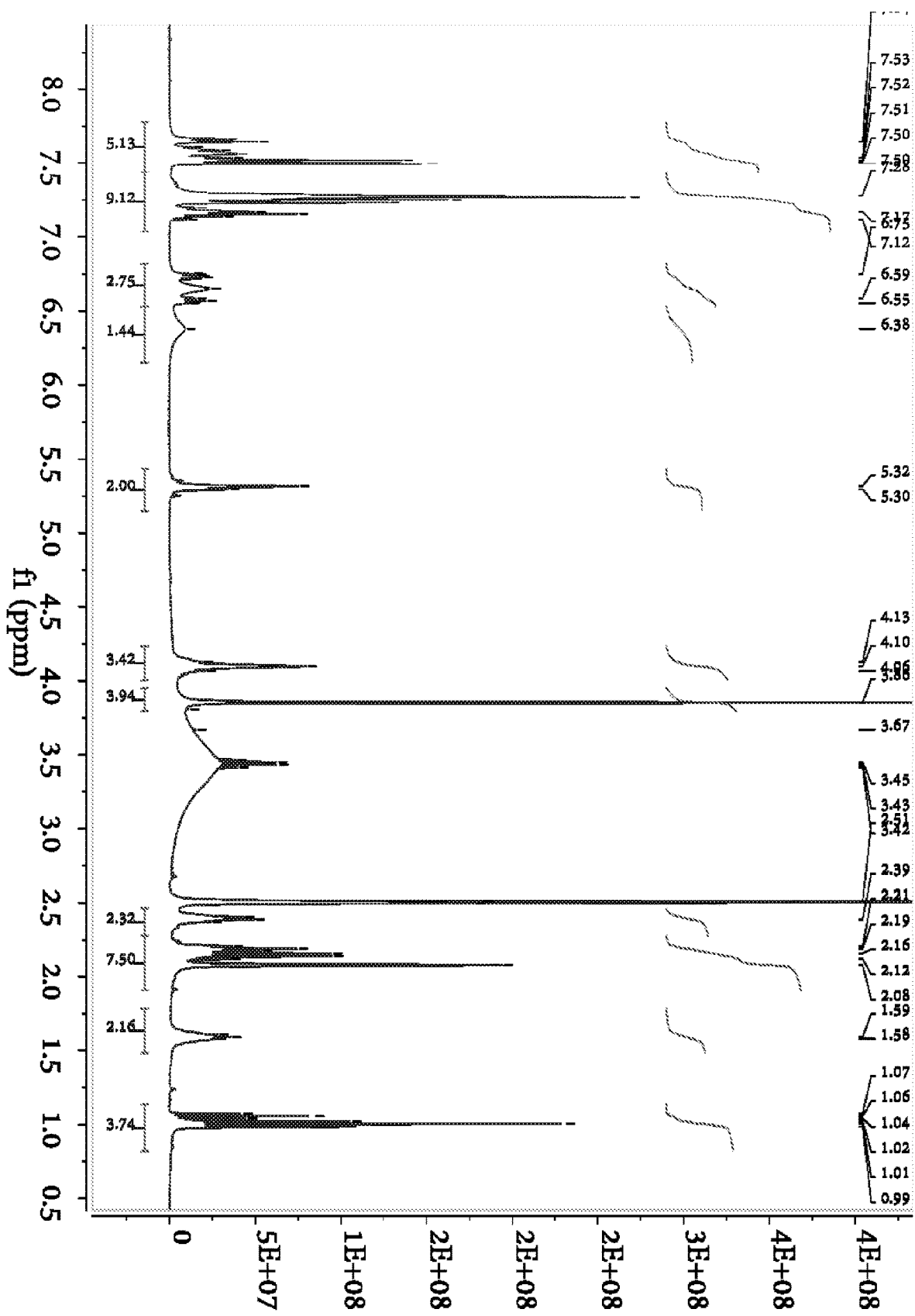
FIG. 11 is a $^1$H-NMR spectrum of the eutectic form A in Example 1 of the present disclosure.
Figure 15:
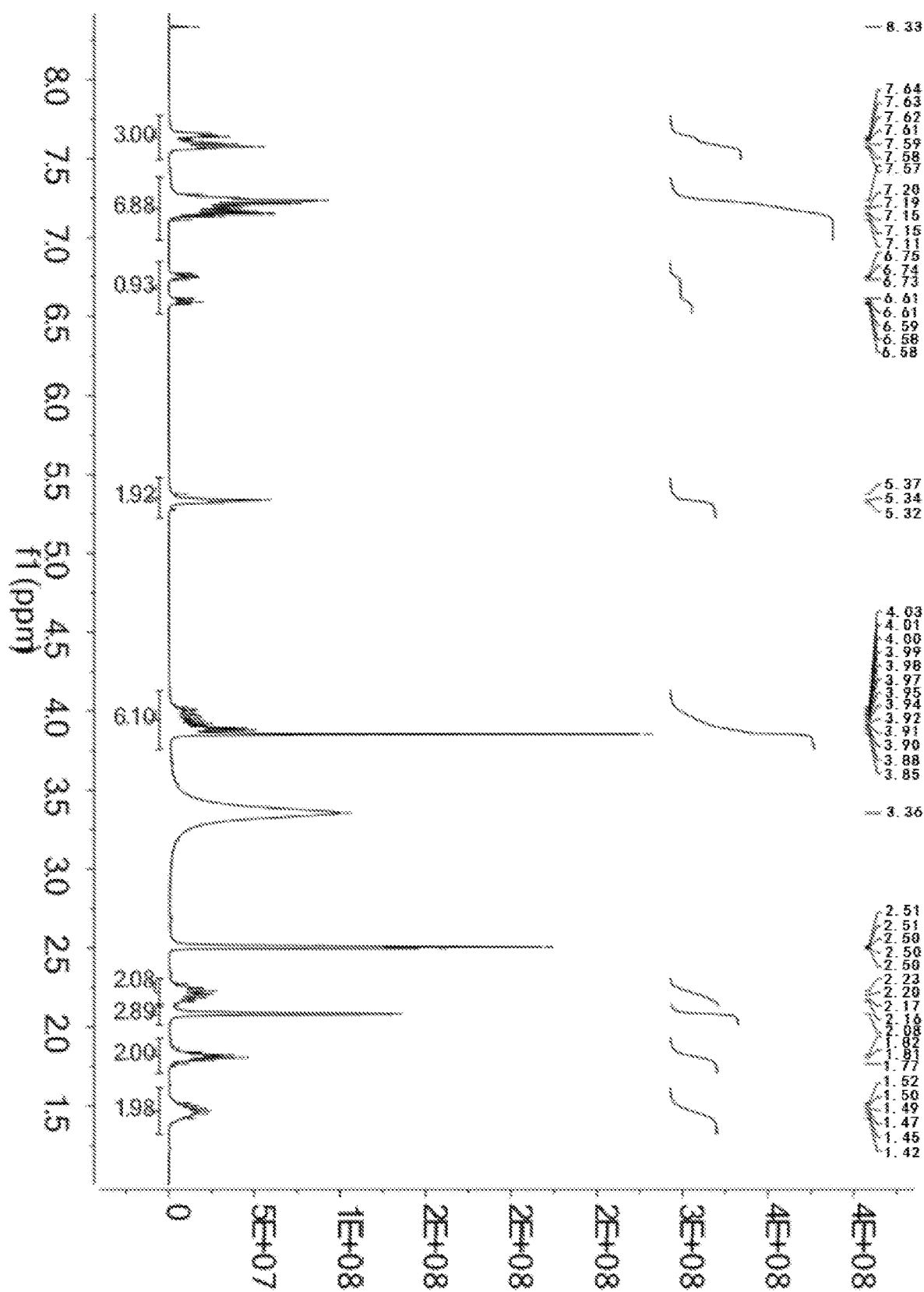
FIG. 15 is a $^1$H-NMR spectrum of the raw drug of Elagolix sodium in Comparative example 1 of the present disclosure.

A $^1$H-NMR spectrum of pyrimethamine is shown in FIG. 10, a $^1$H-NMR spectrum of the eutectic form A is shown in FIG. 11, and a ¹H-NMR spectrum of the raw drug of Elagolix sodium is shown in FIG. 15. The sum of characteristic peaks of the ¹H-NMR spectrum of pyrimethamine and the ¹H-NMR spectrum of the raw drug of Elagolix sodium is similar to but not exactly the same as the ¹H-NMR spectrum of the eutectic form A, and the chemical shifts are slightly shifted. The combination of the ¹H-NMR spectrum and the XRPD pattern proves that Elagolix and pyrimethamine form an eutectic form.

Comparative Example 1 Preparation of Raw Drug of Elagolix Sodium

For comparison purposes, the method disclosed in Example 1 of CN100424078B was used to prepare the raw drug of Elagolix sodium. The specific method included the following steps:

An Elagolix free acid (a raw drug) was purchased from Shanghai Haoyuan Pharmaceutical Co., Ltd. with a chemical purity of more than 98%. 1 g of the Elagolix free acid was dissolved in 30 ml/30 ml THF/water. Solid NaOH (1.6 g) was added, and the resulting mixture was heated at 50° C. overnight, the mixture was cooled to room temperature and the volatiles were removed. Citric acid was added to the aqueous solution until a pH was equal to 3, the solution was extracted with ethyl acetate, and then the solvent was evaporated to obtain 1.96 g of a white gel. The gel was transformed into a sodium salt by a Dowex MSC-1 macroporous strong cation-exchange column, and sublimation drying was conducted under low pressure to obtain the sodium salt, namely Elagolix sodium.

The structure of the raw drug of Elagolix sodium was characterized by nuclear magnetic resonance (¹H-NMR), differential scanning calorimetry (DSC) and thermo gravimetric analysis (TGA), respectively, thereby further confirming the formation of the sodium salt.

① X-Ray Powder Diffraction (XRPD)

X-ray powder diffraction was performed by using the raw drug of Elagolix sodium under the following test conditions:

Determination was performed by using Cu-Kα under a voltage of 40 KV, and a current of 40 mA at a test angle of 3-45°, a step length of 0.02°, and a light tube slit width of 2 mm by using a Dtex detector, and a Japanese Rigaku Uitima IV type X-ray powder diffractometer.

Figure 12:
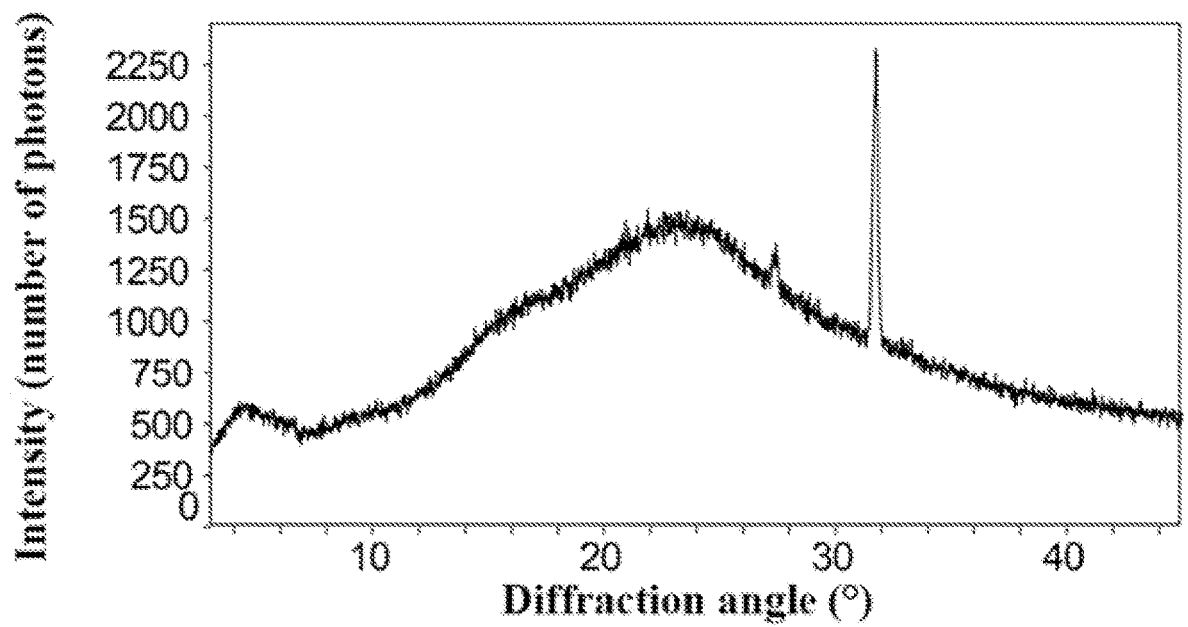
FIG. 12 is an X-ray diffraction pattern of a raw drug of Elagolix sodium in Comparative example 1 of the present disclosure.

The XRPD pattern of the above raw drug of Elagolix sodium is shown in FIG. 12, and it can be seen from FIG. 12 that the raw drug of Elagolix sodium is amorphous.

② DSC Determination

DSC determination was performed by using the raw drug of Elagolix sodium under the following conditions:

Determination was performed by a Q2000 differential scanning calorimeter of TA Instruments Inc, USA, with nitrogen protection, and a heating rate of 10° C./min.

Figure 13:
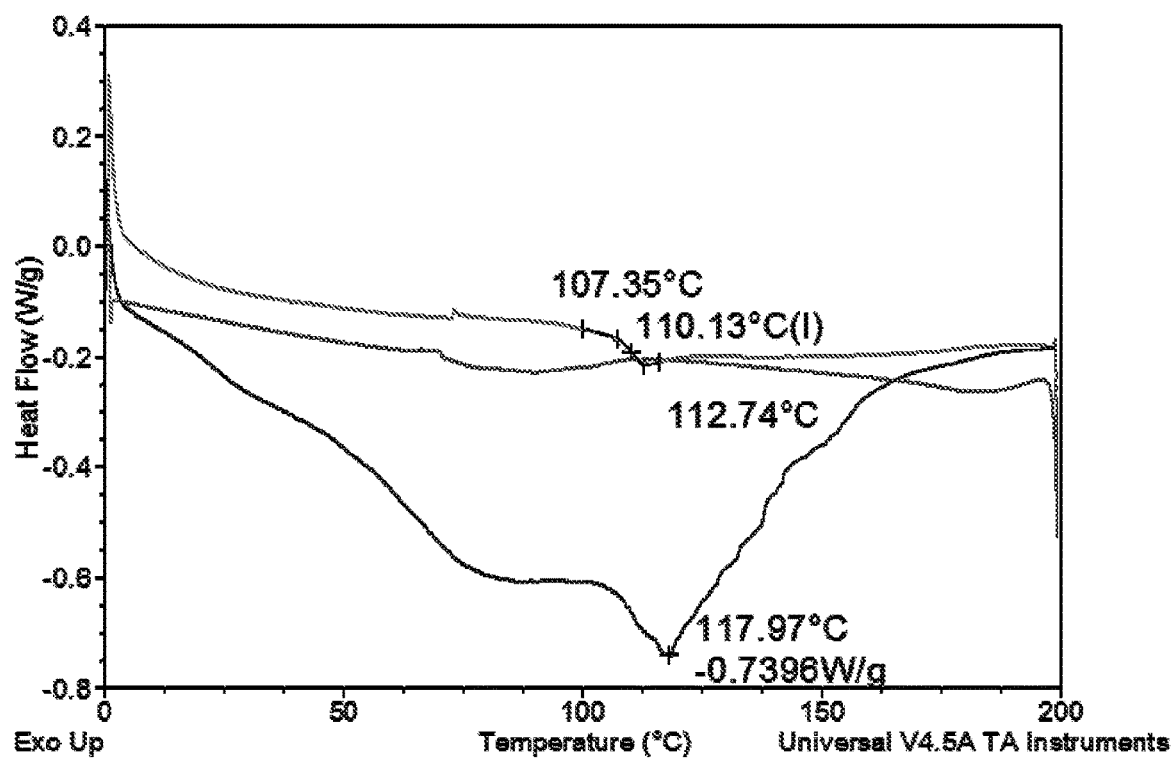
FIG. 13 is a DSC curve of the raw drug of Elagolix sodium in Comparative example 1 of the present disclosure.

The DSC pattern of the raw drug of Elagolix sodium is shown in FIG. 13. It can be seen from FIG. 13 that the raw drug of Elagolix sodium is amorphous, and the glass transition temperature is about 110.1° C.

③ TGA Detection

TGA determination was performed by using the raw drug of Elagolix sodium under the following conditions:

Determination was performed by Q500 of TA Instruments Inc, USA, and the test conditions were as follows: a heating rate was 10° C./min.

Figure 14:
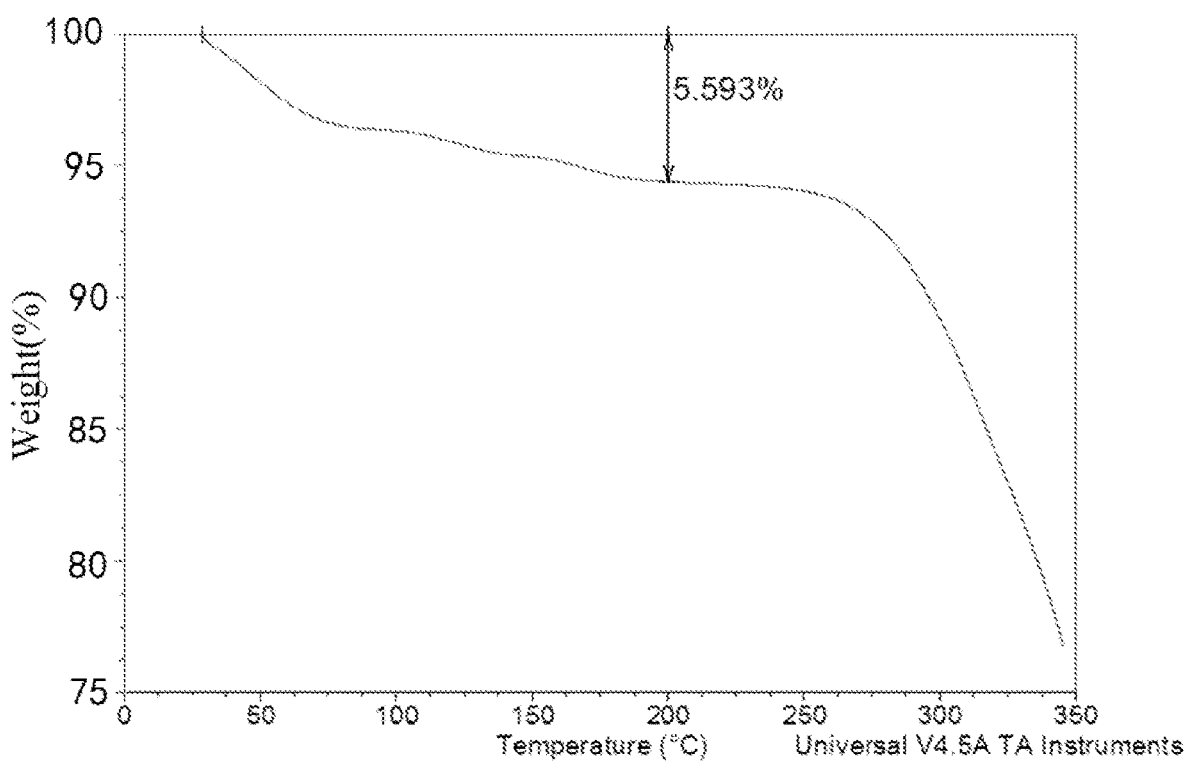
FIG. 14 is a TGA curve of the raw drug of Elagolix sodium in Comparative example 1 of the present disclosure.

The TGA pattern of the raw drug of Elagolix sodium is shown in FIG. 14. It can be seen from FIG. 14 that the weight loss of the raw drug of Elagolix sodium heated to 200° C. is about 5.59%.

④ ¹H-NMR Detection

¹H-NMR detection was performed by using the raw drug of Elagolix sodium, respectively under the following test conditions:

BRUKER AM-400 nuclear magnetic resonance spectrometer, solvent: DMSO-$d_6$.

A ¹H-NMR spectrum of the raw drug of Elagolix sodium is shown in FIG. 15.

Comparative Example 2

33.0 mg of a raw drug of Elagolix sodium was weighed, 1.2 ml of ethanol and 5.5 μl of concentrated hydrochloric acid were added, 5.2 mg of sodium hydroxide was weighed and added thereto, and the obtained mixture was suspended at 50° C. for 24 h, and evaporated to dryness to obtain an oil. The morphology of this sample is difficult to characterize in a solid state, so it is not considered.

Comparative Example 3

33.0 mg of a raw drug of Elagolix sodium was weighed, 1.2 ml of ethanol and 5.5 μl of concentrated hydrochloric acid were added, 15 μl of choline was measured and added thereto, and the obtained mixture was suspended at 50° C. for 24 h, and evaporated to dryness to obtain an oil. The morphology of this sample is difficult to characterize in a solid state, so it is not considered.

Comparative Example 4

Figure 16:
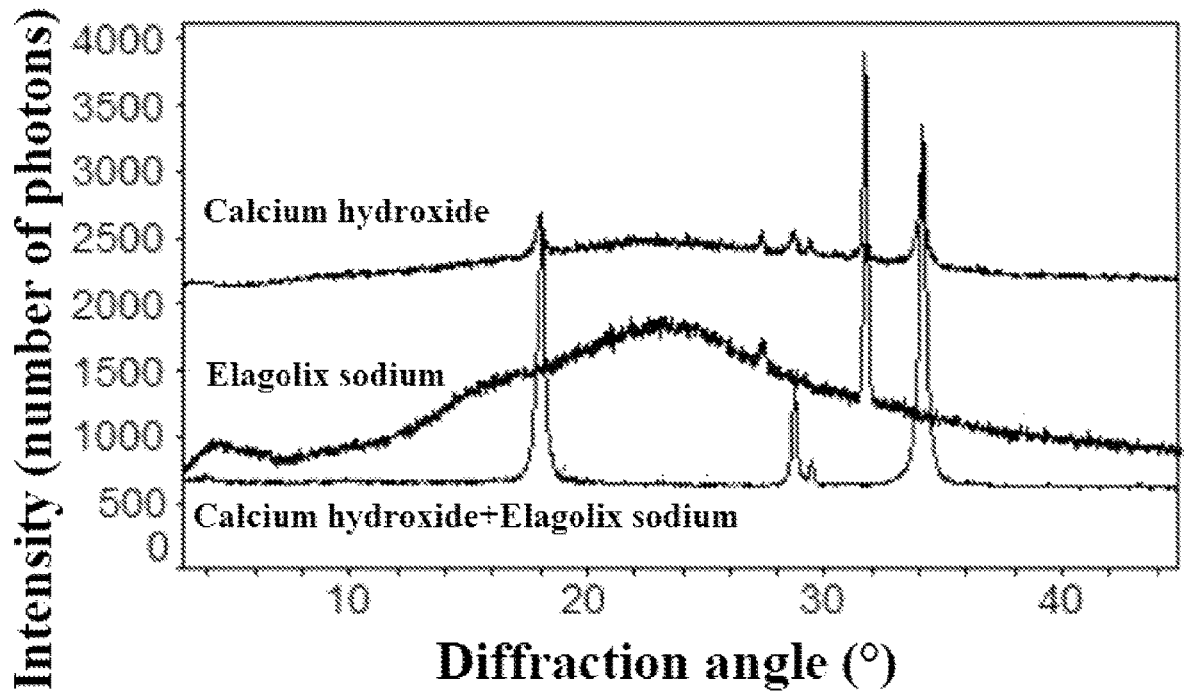
FIG. 16 is a comparative XRPD pattern of substances in Comparative example 4 of the present disclosure, wherein an upper graph is an XRPD pattern of calcium hydroxide, a middle graph is an XRPD pattern of a raw drug of Elagolix sodium, and a lower graph is an XRPD pattern of a solid product prepared in Comparative example 4.

33.0 mg of a raw drug of Elagolix sodium was weighed, 1.2 ml of ethanol and 5.5 μl of concentrated hydrochloric acid were added, 4.9 mg of calcium hydroxide was weighed and added thereto, and the obtained mixture was suspended at 50° C. for 24 h, and evaporated to dryness to obtain a solid. The solid product was characterized by XRPD (using the instrument and test conditions which are the same as those in Example 1), and the XRPD pattern of the solid product was compared with the XRPD patterns of the raw drug of Elagolix sodium and calcium hydroxide, as shown in FIG. 16. From the XRPD results, the product was a physical mixture of the raw drug of Elagolix sodium and a ligand, and no eutectic was formed, so it is not considered.

Comparative Example 5

33.0 mg of a raw drug of Elagolix sodium was weighed, 1.2 ml of ethanol and 5.5 μl of concentrated hydrochloric acid were added, 6 μl of diethylamine was measured and added thereto, and the obtained mixture was suspended at 50° C. for 24 h, and evaporated to dryness to obtain an oil. The morphology of this sample is difficult to characterize in a solid state, so it is not considered.

Comparative Example 6

33.0 mg of a raw drug of Elagolix sodium was weighed, 1.2 ml of ethanol and 5.5 μl of concentrated hydrochloric acid were added, 4 μl of ethanolamine was measured and added thereto, and the obtained mixture was at 50° C. for 24 h, and evaporated to dryness to obtain an oil. The morphology of this sample is difficult to characterize in a solid state, so it is not considered.

Comparative Example 7

33.0 mg of a raw drug of Elagolix sodium was weighed, 1.2 ml of ethanol and 5.5 μl of concentrated hydrochloric acid were added, 6.0 mg of imidazole was weighed and added thereto, and the obtained mixture was suspended at 50° C. for 24 h, and evaporated to dryness to obtain an oil. The morphology of this sample is difficult to characterize in a solid state, so it is not considered.

Comparative Example 8

Figure 17:
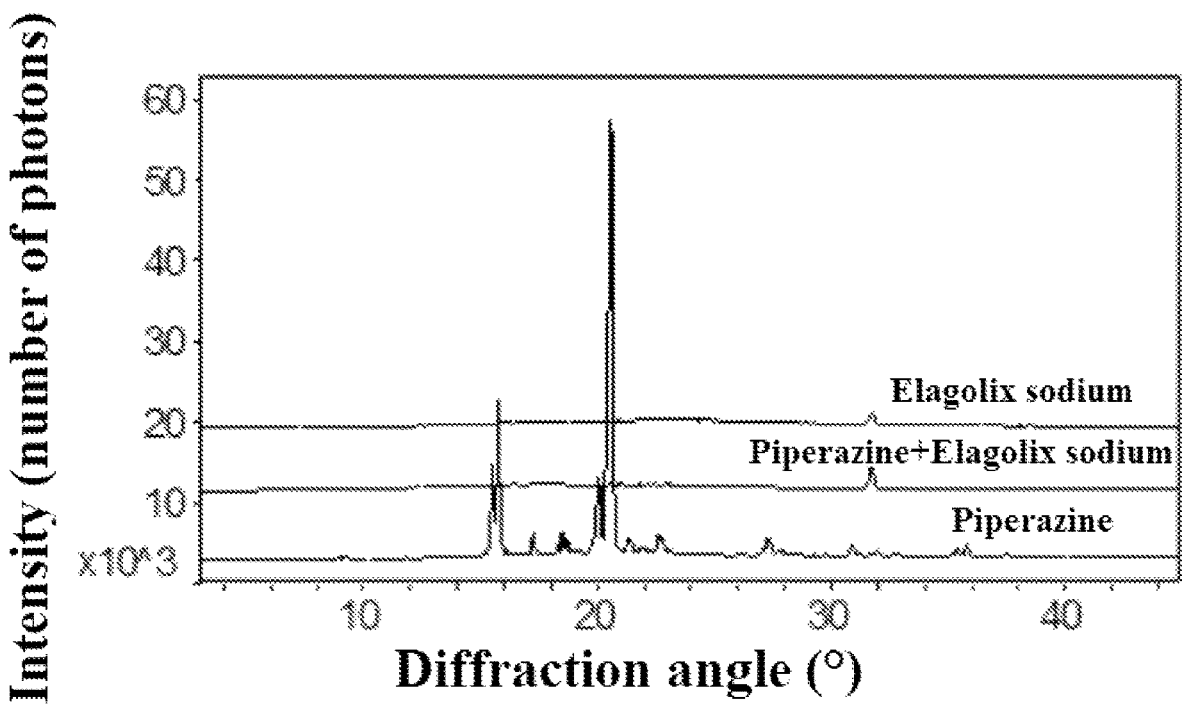
FIG. 17 is a comparative XRPD pattern of substances in Comparative example 8 of the present disclosure, wherein an upper pattern is an XRPD pattern of a raw drug of Elagolix sodium, a middle pattern is an XRPD pattern of a solid product prepared in Comparative example 8, and a lower pattern is an XRPD pattern of piperazine.

33.0 mg of a raw drug of Elagolix sodium was weighed, 1.2 ml of ethanol and 5.5 µl of concentrated hydrochloric acid were added, 4.9 mg of piperazine was weighed and added thereto, and the obtained mixture was suspended at 50° C. for 24 h, and evaporated to dryness to obtain a solid. The solid product was characterized by XRPD (using the instrument and test conditions which are the same as those in Example 1), and the XRPD pattern of the solid product was compared with the XRPD patterns of the raw drug of Elagolix sodium and piperazine, as shown in FIG. 17. From the XRPD results, the product was similar to the raw drug of Elagolix sodium, and no eutectic was formed, so it is not considered.

Comparative Example 9

11.5 mg of N-methyl-D-glucosamine was weighed, and 0.2 ml of water was added to obtain an aqueous solution of N-methyl-D-glucosamine for later use, 33.0 mg of a raw drug of Elagolix sodium was weighed, 1.2 ml of ethanol and 5.5 µl of concentrated hydrochloric acid were added, the above-mentioned aqueous N-methyl-D-glucosamine solution was added, and the obtained mixture was stirred for 12 h, and evaporated to dryness to obtain an oil. The morphology of this sample is difficult to characterize in a solid state, so it is not considered.

Comparative Example 10

Figure 18:
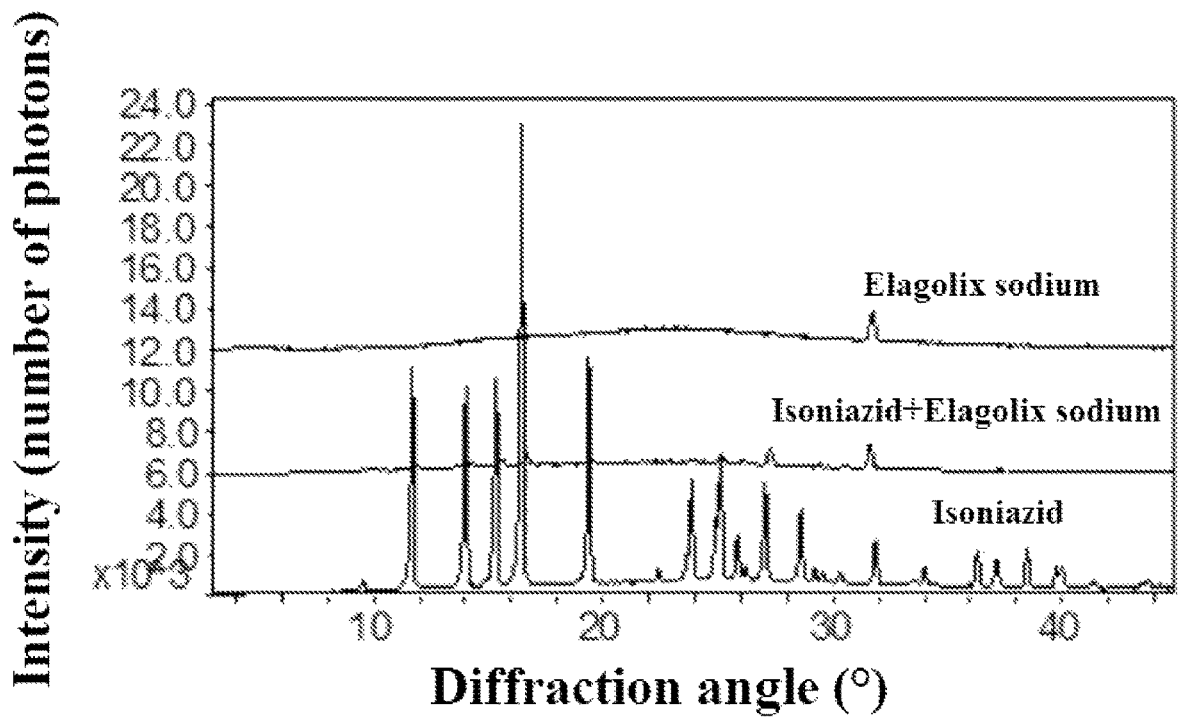
FIG. 18 is a comparative XRPD pattern of substances in Comparative example 10 of the present disclosure, wherein an upper pattern is an XRPD pattern of a raw drug of Elagolix sodium, a middle pattern is an XRPD pattern of a solid product prepared in Comparative example 10, and a lower pattern is an XRPD pattern of isoniazid.

7.6 mg of isoniazid was weighed, and 0.2 ml of water was added to obtain an aqueous isoniazid solution for later use, 33.0 mg of a raw drug of Elagolix sodium was weighed, 1.2 ml of ethanol and 5.5 µl of concentrated hydrochloric acid were added, the above aqueous isoniazid solution was added, and the obtained mixture was stirred for 12 h, and evaporated to dryness to obtain a solid. The solid product was characterized by XRPD (using the instrument and test conditions which are the same as those in Example 1), and the XRPD pattern of the solid product was compared with the XRPD patterns of the raw drug of Elagolix sodium and isoniazid, as shown in FIG. 18. From the XRPD results, the product was a physical mixture of the raw drug of Elagolix sodium and a ligand, and no eutectic was formed, so it is not considered.

Comparative Example 11

7.0 mg of isonicotinamide was weighed, and 0.2 ml of water was added to obtain an aqueous isonicotinamide solution for later use, 33.0 mg of a raw drug of Elagolix sodium was weighed, 1.2 ml of ethanol and 5.5 µl of concentrated hydrochloric acid were added, the above aqueous isonicotinamide solution was added, and the obtained mixture was stirred for 12 h, and evaporated to dryness to obtain an oil. The morphology of this sample is difficult to characterize in a solid state, so it is not considered.

Comparative Example 12

8.2 mg of salicylamide was weighed, and 0.2 ml of water was added to obtain an aqueous salicylamide solution for later use, 33.0 mg of a raw drug of Elagolix sodium was weighed, 1.2 ml of ethanol and 5.5 µl of concentrated hydrochloric acid were added, the above aqueous salicylamide solution was added, and the obtained mixture was stirred for 12 h, and evaporated to dryness to obtain an oil. The morphology of this sample is difficult to characterize in a solid state, so it is not considered.

Comparative Example 13

Figure 19:
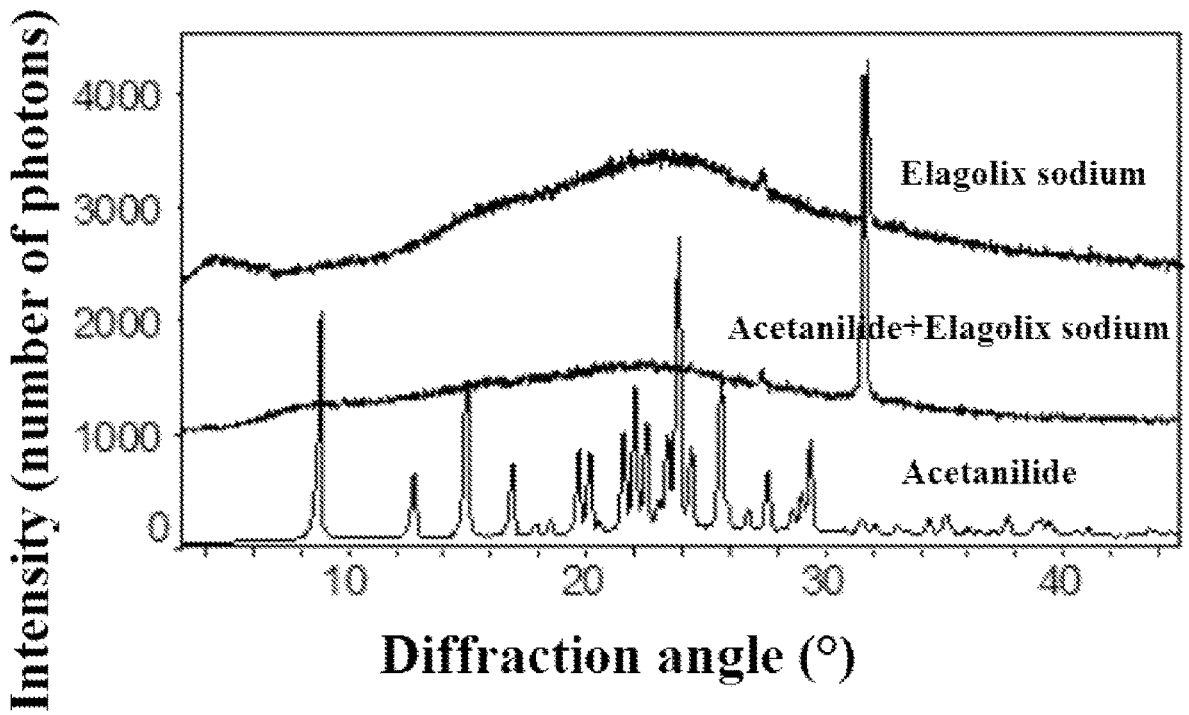
FIG. 19 is a comparative XRPD pattern of substances in Comparative example 13 of the present disclosure, wherein an upper pattern is an XRPD pattern of a raw drug of Elagolix sodium, a middle pattern is an XRPD pattern of a solid product prepared in Comparative example 13, and a lower pattern is an XRPD pattern of acetanilide.

8.2 mg of acetanilide was weighed, and 0.2 ml of water was added to obtain an aqueous acetanilide solution for later use, 33.0 mg of a raw drug of Elagolix sodium was weighed, 1.2 ml of ethanol and 5.5 µl of concentrated hydrochloric acid were added, the above-mentioned aqueous acetanilide solution was added, and the obtained mixture was stirred for 12 h, and evaporated to dryness to obtain a solid. The solid product was characterized by XRPD (using the instrument and test conditions which are the same as those in Example 1), and the XRPD pattern of the solid product was compared with the XRPD pattern of the raw drug of Elagolix sodium, as shown in FIG. 19. From the XRPD results, the product did not form an eutectic, so it is not considered.

Comparative Example 14

Figure 20:
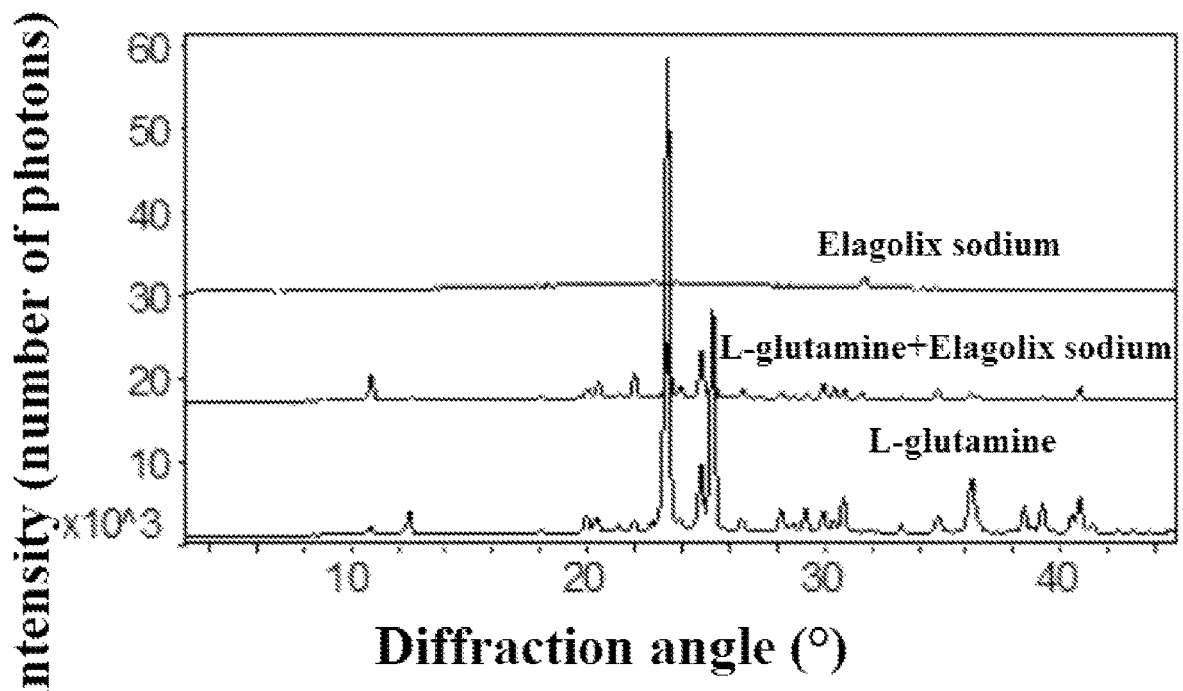
FIG. 20 is a comparative XRPD pattern of substances in Comparative example 14 of the present disclosure, wherein an upper pattern is an XRPD pattern of a raw drug of Elagolix sodium, a middle pattern is an XRPD pattern of a solid product prepared in Comparative example 14, and a lower pattern is an XRPD pattern of L-glutamine.

8.1 mg of L-glutamine was weighed, and 0.2 ml of water was added to obtain an aqueous solution of L-glutamine for later use, 33.0 mg of a raw drug of Elagolix sodium was weighed, 1.2 ml of ethanol and 5.5 µl of concentrated hydrochloric acid were added, the above aqueous solution of L-glutamine was added, and the obtained mixture was stirred for 12 h, and filtered to obtain a solid. The solid product was characterized by XRPD (using the instrument and test conditions which are the same as those in Example 1), and the XRPD pattern of the solid product was compared with the XRPD patterns of the raw drug of Elagolix sodium and L-glutamine, as shown in FIG. 20. From the XRPD results, the product was a physical mixture of the raw drug of Elagolix sodium and a ligand, and no eutectic was formed, so it is not considered.

Comparative Example 15

3.6 mg of urea was weighed, and 0.2 ml of water was added to obtain an aqueous solution of urea for later use, 33.0 mg of a raw drug of Elagolix sodium was weighed, 1.2 ml of ethanol and 5.5 µl of concentrated hydrochloric acid were added, the above aqueous solution of urea was added, and the obtained mixture was stirred for 12 h, and evaporated to dryness to obtain an oil. The morphology of this sample is difficult to characterize in a solid state, so it is not considered.

Comparative Example 16

10.6 mg of 1,2-bis(4-pyridylethane) was weighed, and 0.2 ml of water was added to obtain an aqueous solution of 1,2-bis(4-pyridyl)ethane for later use, 33.0 mg of a raw drug of Elagolix sodium was weighed, 1.2 ml of ethanol and 5.5 µl of concentrated hydrochloric acid were added, the above-mentioned aqueous solution of 1,2-bis(4-pyridyl)ethane, and the obtained mixture was stirred for 12 h, and evaporated to dryness to obtain an oil. The morphology of this sample is difficult to characterize in a solid state, so it is not considered.

Comparative Example 17

Figure 21:
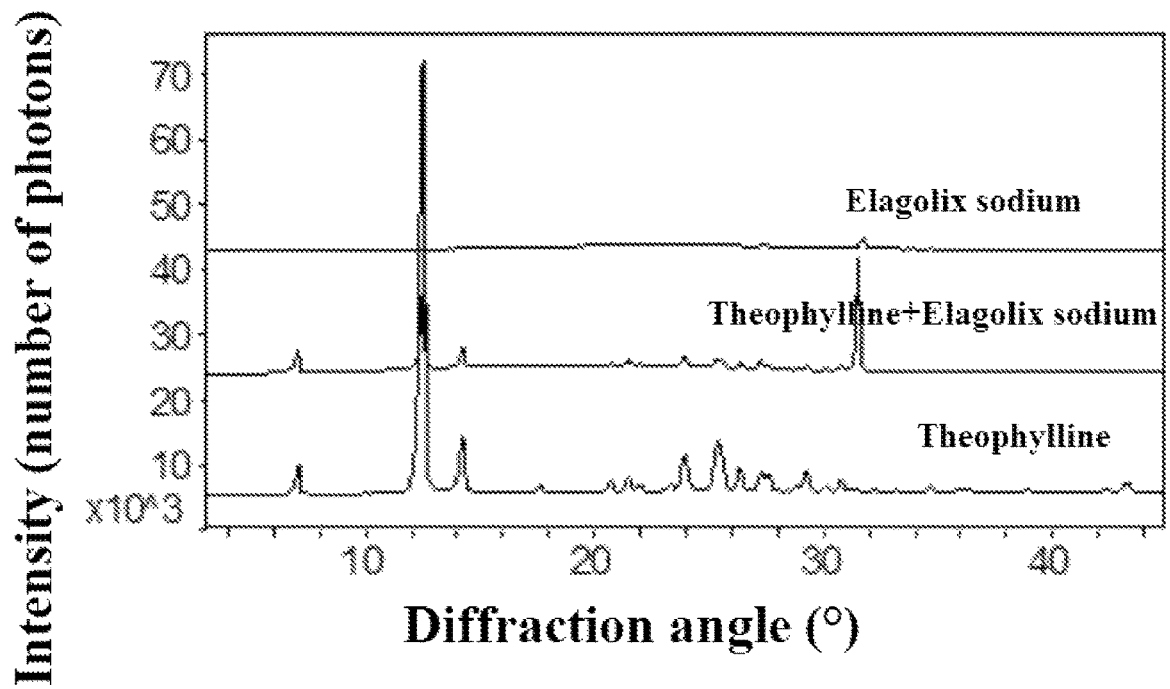
FIG. 21 is a comparative XRPD pattern of substances in Comparative example 17 of the present disclosure, wherein an upper pattern is an XRPD pattern of a raw drug of Elagolix sodium, a middle pattern is an XRPD pattern of a solid product prepared in Comparative example 17, and a lower pattern is an XRPD pattern of theophylline.

10.3 mg of theophylline was weighed, and 0.2 ml of water was added to obtain an aqueous theophylline solution for later use, 33.0 mg of a raw drug of Elagolix sodium was weighed, 1.2 ml of ethanol and 5.5 µl of concentrated hydrochloric acid were added, the above-mentioned aqueous theophylline solution was added, and the obtained mixture was stirred for 12 h, and evaporated to obtain a solid. The solid product was characterized by XRPD (using the instrument and test conditions which are the same as those in Example 1), and the XRPD pattern of the solid product was compared with the XRPD patterns of the raw drug of Elagolix sodium and theophylline, as shown in FIG. 21. From the XRPD results, the product was a physical mixture of the raw drug of Elagolix sodium and a ligand, and no eutectic was formed, so it is not considered.

Comparative Example 18

8.5 mg of isoquinoline was weighed, and 0.2 ml of water was added to obtain an aqueous isoquinoline solution for later use, 33.0 mg of a raw drug of Elagolix sodium was weighed, 1.2 ml of ethanol and 5.5 µl of concentrated hydrochloric acid were added, the above aqueous isoquinoline solution was added, and the obtained mixture was stirred for 12 h, and evaporated to dryness to obtain an oil. The morphology of this sample is difficult to characterize in a solid state, so it is not considered.

Comparative Example 19

9.5 mg of sulfonamide was weighed, and 0.2 ml of water was added to obtain an aqueous sulfonamide solution for later use, 33.0 mg of a raw drug of Elagolix sodium was weighed, 1.2 ml of ethanol and 5.5 µl of concentrated hydrochloric acid were added, the above aqueous sulfonamide solution was added, and the obtained mixture was stirred for 12 h, and evaporated to dryness to obtain an oil. The morphology of this sample is difficult to characterize in a solid state, so it is not considered.

Comparative Example 20

14.5 mg of sulfamerazine was weighed, and 0.2 ml of water was added to obtain an aqueous sulfamerazine solution for later use, 33.0 mg of a raw drug of Elagolix sodium was weighed, 1.2 ml of ethanol and 5.5 µl of concentrated hydrochloric acid were added, the above aqueous sulfamerazine solution, and the obtained mixture was stirred for 12 h, and evaporated to dryness to obtain an oil. The morphology of this sample is difficult to characterize in a solid state, so it is not considered.

Comparative Example 21

15.3 mg of sulfadimidine was weighed, and 0.2 ml of water was added to obtain an aqueous sulfadimidine solution for later use, 33.0 mg of a raw drug of Elagolix sodium was weighed, 1.2 ml of ethanol and 5.5 µl of concentrated hydrochloric acid were added, the above aqueous sulfadimidine solution was added, and the obtained mixture was stirred for 12 h, and evaporated to dryness to obtain an oil. The morphology of this sample is difficult to characterize in a solid state, so it is not considered.

Comparative Example 22

6.9 mg of trimethylolaminomethane was weighed, and 0.2 ml of water was added to obtain an aqueous trimethylolaminomethane solution for later use, 33.0 mg of a raw drug of Elagolix sodium was weighed, 1.2 ml of ethanol and 5.5 µl of concentrated hydrochloric acid were added, the above-mentioned aqueous trimethylolaminomethane solution was added, and the obtained mixture was stirred for 12 h, and evaporated to dryness to obtain an oil. The morphology of this sample is difficult to characterize in a solid state, so it is not considered.

Comparative Example 23

6.2 mg of succinimide was weighed, and 0.2 ml of water was added to obtain an aqueous succinimide solution for later use, 33.0 mg of a raw drug of Elagolix sodium was weighed, 1.2 ml of ethanol and 5.5 µl of concentrated hydrochloric acid were added, the above aqueous succinimide solution was added, and the obtained mixture was stirred for 12 h, and evaporated to dryness to obtain an oil. The morphology of this sample is difficult to characterize in a solid state, so it is not considered.

The above examples are only examples for clear explanation, not a limitation of the embodiments. For those of ordinary skill in the art, other different forms of changes or variations can be made on the basis of the above description. It is unnecessary and impossible to enumerate all the embodiments here. The obvious changes or variations derived therefrom are still within the protection scope of the present disclosure.

What is claimed is:

1. An eutectic form A of Elagolix and pyrimethamine, wherein an X-ray powder diffraction of the eutectic form A using Cu-Kα radiation has characteristic peaks at 2θ angles of 8.1±0.2°, 12.2±0.2°, 13.3±0.2° and 21.1±0.2°.

2. The eutectic form A of Elagolix and pyrimethamine according to claim 1, wherein the X-ray powder diffraction of the eutectic form A using Cu-Kα radiation also has a characteristic peak at 2θ angle of 24.4±0.2°.

3. The eutectic form A of Elagolix and pyrimethamine according to claim 1, wherein the X-ray powder diffraction of the eutectic form A using Cu-Kα radiation also has characteristic peaks at 2θ angles of 16.2±0.2° and 22.0±0.2°.

4. The eutectic form A of Elagolix and pyrimethamine according to claim 1, wherein the X-ray powder diffraction of the eutectic form A using Cu-Kα radiation also has characteristic peaks at 2θ angles of 28.1±0.2° and 31.7±0.2°.

5. The eutectic form A of Elagolix and pyrimethamine according to claim 1, wherein the eutectic form A has characteristic peaks in its X-ray powder diffraction pattern comprising:

| 2θ (±0.2°) | d (Å) | I % |
|---|---|---|
| 8.1 | 10.9 | 9.6 |
| 12.2 | 7.3 | 7 |
| 13.3 | 6.7 | 37.3 |
| 21.1 | 4.2 | 47.3 |
| 22.0 | 4.0 | 4.1 |
| 24.4 | 3.6 | 86.4 |
| 31.7 | 2.8 | 100. |

6. The eutectic form A of Elagolix and pyrimethamine according to claim 1, wherein the eutectic form A has characteristic peaks in its X-ray powder diffraction pattern comprising:

| 2θ (±0.2°) | d (Å) | I % |
|---|---|---|
| 8.074 | 10.9408 | 9.6 |
| 12.176 | 7.2631 | 7 |
| 13.26 | 6.6715 | 37.3 |
| 15.838 | 5.5909 | 8 |
| 16.157 | 5.4813 | 9.3 |
| 21.138 | 4.1996 | 47.3 |
| 22.017 | 4.0338 | 4.1 |
| 23.9 | 3.72 | 11.3 |
| 24.44 | 3.6392 | 86.4 |
| 26.58 | 3.3508 | 24 |
| 27.361 | 3.2569 | 8.9 |
| 28.08 | 3.1752 | 20.5 |
| 31.699 | 2.8204 | 100 |
| 32.163 | 2.7807 | 14.4 |
| 33.143 | 2.7007 | 5.1 |
| 34.539 | 2.5947 | 8.6 |
| 37.223 | 2.4136 | 8.6 |
| 42.52 | 2.1243 | 5.5. |

7. The eutectic form A of Elagolix and pyrimethamine according to claim 1, wherein the eutectic form A has an X-ray powder diffraction pattern substantially as shown in FIG. 7A.

8. The eutectic form A of Elagolix and pyrimethamine according to claim 1, wherein a differential scanning calorimetry curve of the eutectic form A has a first endothermic peak and a second endothermic peak, wherein the first endothermic peak is at a temperature of 69.49±2° C., and the second endothermic peak is at a temperature of 204.78±2° C.

9. The eutectic form A of Elagolix and pyrimethamine according to claim 1, wherein the eutectic form A has a differential scanning calorimetry curve substantially as shown in FIG. 8.

10. The eutectic form A of Elagolix and pyrimethamine according to claim 1, wherein a thermo gravimetric analysis curve of the eutectic form A has a thermal weight loss of less than 6.2% before 193° C.

11. The eutectic form A of Elagolix and pyrimethamine according to claim 1, wherein the eutectic form A has a thermo gravimetric analysis curve substantially as shown in FIG. 9.

12. A method for preparing the eutectic form A of Elagolix and pyrimethamine according to claim 1, the method comprising: dissolving a raw drug of Elagolix sodium in an organic solvent, adding a concentrated hydrochloric acid thereto, adding an aqueous solution of pyrimethamine, stirring, filtering, and drying to obtain an eutectic.

13. The method according to claim 12, wherein a molar ratio of the raw drug of Elagolix sodium to pyrimethamine is in a range of from 1.0:1.1 to 1.0:1.5.

14. A pharmaceutical composition, comprising the eutectic form A of Elagolix and pyrimethamine according to claim 1 and a pharmaceutically acceptable excipient.

15. A method for the treatment of a sex hormone-related disease state, a gonadotropin releasing hormone-related disease state, infertility, lupus erythematosus, irritable bowel syndrome, premenstrual syndrome, hirsutism, short stature, or sleep disorder in an individual in need thereof, the method comprising administering to the individual a pharmaceutically effective amount of the eutectic form A according to claim 1, or a pharmaceutical composition comprising said eutectic form A and a pharmaceutically acceptable excipient.

16. The method according to claim 15, wherein the sex hormone-related disease state is cancer, benign prostatic hypertrophy, or uterine fibroids.

17. The method according to claim 15, wherein the sex hormone-related disease state is endometriosis, polycystic ovary disease, uterine leiomyoma, or precocious puberty.

18. The method according to claim 16, wherein the cancer is prostate cancer, uterine cancer, breast cancer, or pituitary gonadotropic cell adenoma.

* * * * *